US012734159B2

(12) United States Patent
Sarraf et al.

(10) Patent No.: US 12,734,159 B2
(45) Date of Patent: Sep. 15, 2026

(54) METHODS OF TREATING SPINAL CORD INJURY OR DAMAGE

(71) Applicant: Spinogenix, Inc., La Jolla, CA (US)

(72) Inventors: Stella T. Sarraf, Beverly Hills, CA (US); Vincent F. Simmon, San Diego, CA (US); Peter W. Vanderklish, San Diego, CA (US)

(73) Assignee: Spinogenix, Inc., Los Angeles, CA (US)

( * ) Notice: Subject to any disclaimer, the term of this patent is extended or adjusted under 35 U.S.C. 154(b) by 453 days.

(21) Appl. No.: 18/277,901

(22) PCT Filed: Feb. 18, 2022

(86) PCT No.: PCT/US2022/016936
§ 371 (c)(1),
(2) Date: Aug. 18, 2023

(87) PCT Pub. No.: WO2022/178224
PCT Pub. Date: Aug. 25, 2022

(65) Prior Publication Data

US 2024/0156791 A1 May 16, 2024

Related U.S. Application Data

(60) Provisional application No. 63/152,174, filed on Feb. 22, 2021, provisional application No. 63/287,710, filed on Dec. 9, 2021.

(51) Int. Cl.

| | |
|---|---|
| ***A61K 31/428*** | (2006.01) |
| ***A61K 31/4184*** | (2006.01) |
| ***A61K 31/423*** | (2006.01) |
| ***A61K 31/443*** | (2006.01) |
| ***A61K 31/4439*** | (2006.01) |
| ***A61P 25/00*** | (2006.01) |

(52) U.S. Cl.
CPC ........ *A61K 31/428* (2013.01); *A61K 31/4184* (2013.01); *A61K 31/423* (2013.01); *A61K 31/443* (2013.01); *A61K 31/4439* (2013.01); *A61P 25/00* (2018.01)

(58) Field of Classification Search
CPC .............. A61K 31/428; A61K 31/4184; A61K 31/423; A61K 31/443; A61K 31/4439; A61P 43/00; A61P 25/00
See application file for complete search history.

(56) References Cited

U.S. PATENT DOCUMENTS

| | | | |
|---|---|---|---|
| 5,534,532 | A | 7/1996 | Groneberg et al. |
| 6,576,654 | B1 | 6/2003 | Macias |
| 7,666,886 | B2 | 2/2010 | Yang et al. |
| 8,741,883 | B2 | 6/2014 | Yang et al. |
| 10,675,273 | B2 | 6/2020 | Yang |
| 11,117,878 | B2 * | 9/2021 | Sarraf .................. C07D 277/66 |
| 2006/0154932 | A1 | 7/2006 | Hathaway et al. |
| 2009/0028787 | A1 | 1/2009 | Gravenfors et al. |
| 2012/0253047 | A1 | 10/2012 | Allegrini et al. |
| 2014/0024705 | A1 | 1/2014 | Danishefsky et al. |
| 2014/0080843 | A1 | 3/2014 | Huang et al. |
| 2015/0299191 | A1 | 10/2015 | Huang et al. |
| 2015/0366776 | A1 | 12/2015 | Chung et al. |
| 2019/0000811 | A1 | 1/2019 | Yang |
| 2019/0046538 | A1 | 2/2019 | Rotolo et al. |
| 2021/0330646 | A1 | 10/2021 | Sarraf et al. |
| 2022/0017477 | A1 | 1/2022 | Sarraf et al. |
| 2022/0106330 | A1 | 4/2022 | Sarraf et al. |

FOREIGN PATENT DOCUMENTS

| | | | |
|---|---|---|---|
| WO | WO 2007/091313 | A1 | 8/2007 |
| WO | WO 2013/013240 | A2 | 1/2013 |
| WO | WO 2013/037411 | A1 | 3/2013 |
| WO | WO 2014/031732 | A2 | 2/2014 |
| WO | WO 2014/134287 | A1 | 9/2014 |
| WO | WO 2015/127125 | A1 | 8/2015 |
| WO | WO 2017/120198 | A1 | 7/2017 |
| WO | WO 2019/005682 | A1 | 1/2019 |
| WO | WO 2019/028164 | A1 | 2/2019 |
| WO | WO 2020/046991 | A1 | 3/2020 |
| WO | WO 2020/160332 | A1 | 8/2020 |

OTHER PUBLICATIONS

Tan et al., "Spinal cord injury, dendritic spine remodeling, and spinal memory mechanisms", Experimental Neurology, vol. 235, No. 1, pp. 142-151 (2012).*

Ciapetti, et al. Molecular Variations Based on Isosteric Replacements. The Practice of Medicinal Chemistry. Elsevier, Amsterdam, NL. Jan. 1, 2008; Chapter 8: pp. 181-241.

Cifelli, et al. Benzothiazole Amphiphiles Ameliorate Amyloid B-Related Cell Toxicity and Oxidative Stress. ACS Chem. Neurosci. 2016, 7, 6, 682-688.

Cifelli, et al. Benzothiazole Amphiphiles Promote the Formation of Dendritic of dendritic spines in primary hippocampal neurons. Journal of Biological Chemistry. Jun. 3, 2016; 291(23):11981-11992.

Croft, et al. Abstract LB-228: Identifying small molecule inhibitors of Fascin 1 using fragment-based drug discovery, Cancer Research, Jul. 2017 vol. 77, Issue 13 Supplement; DOI: 10.1158/1538-7445. AM2017-LB-228.

European Search Report & Opinion dated May 3, 2022 for 19854074. 2. 16 pages.

(Continued)

*Primary Examiner* — Kevin E Weddington

(74) *Attorney, Agent, or Firm* — Sheppard Mullin Richter & Hampton LLP

(57) ABSTRACT

In some embodiments, a method of treating spinal cord injury or damage, or a complication thereof, in a patient is provided, comprising administering to a patient in need thereof a therapeutically effective amount of a compound of formula I, Ia, Ik, or II.

17 Claims, 1 Drawing Sheet

(56) References Cited

OTHER PUBLICATIONS

Extended European Search Report and Search Opinion dated Mar. 31, 2021 for EP Application No. 18840208.5. 12 pages.
Habib, L.K. et al. (Dec. 10, 2010, e-published Oct. 5, 2010). "Inhibitors of catalase- amyloid interactions protect cells from beta-amyloid-induced oxidative stress and toxicity," J Biol Chem 285(50):38933-38943.
Han et al., "Improving fascin inhibitors to block tumor cell migration and metastasis," Molecular Oncology, 2016, vol. 10, pp. 966-960.
Huang et al., Structural Insights into the Induced-fit Inhibition of Fascin by a Small-Molecule Inhibitor, Journal of Molecular Biology 2018; 430(9):1324-1335.
Huang, et al. Inhibition of cholinesterase activity and amyloid aggregation by berberine-phenyl-benzoheterocyclic and tacrine-phenylbenzoheterocyclic hybrids. Bioorganic & Medicinal Chemistry. May 1, 2012; 20(3):3038-3048.
Inbar, P. et al. (Oct. 2006). "Oligo(ethylene glycol) derivatives of thioflavin T as inhibitors of protein-amyloid interactions," ChemBioChem 7(10):1563-1566.
International Search Report & Written Opinion dated Apr. 1, 2020 for PCT/US2020/015967. 21 pages.
International Search Report & Written Opinion dated Sep. 12, 2018 for PCT/US2018/044852. 9 pages.
International Search Report and Written Opinion for International Application No. PCT/US2019/048408 dated Oct. 25, 2019. 12 pages.
International Search Report and Written Opinioned dated Aug. 18, 2022 for PCT Application No. PCT/US2022/021507. 14 pages.
International Search Report and Written Opinioned dated Mar. 30, 2017 for PCT Application No. PCT/US2017/012139, 12 pages.
Kazemi, et al. A mild and efficient procedure for the synthesis of ethers from various alkyl halides. Iran. Chem. Commun. 1 (2013) 43-50.
Lee, N.J. et al. (Feb. 2016, e-published Dec. 8, 2015). "Hexa (ethylene glycol) derivative of benzothiazole aniline promotes dendritic spine formation through the RasGRF1- Ras dependent pathway," Biochim Biophys Acta 1862(2):284-295.
McGill. Alzheimers's disease: neuronal loss very limited. Newsroom—McGill University. Jan. 2018.
Megill, A. et al. (May 29, 2013). "A tetra(ethylene glycol) derivative of benzothiazole aniline enhances Ras-mediated spinogenesis," J Neurosci 33(22):9306-9318.
Nozaki, et al. Drug development chemistry. Kagaku Dojin. Jul. 1, 1995; 98-99.
O'Dell et al., "Association of Aβ deposition and regional synaptic density in early Alzheimer's disease: a PET imaging study with [11C]UCB-J," Alzheimer's Research & Therapy, 2021, vol. 13, No. 11, 12 pages.
Prangkio, P. et al. (2012, e-published Oct. 15, 2012). "Multivariate analyses of amyloid-beta oligomer populations indicate a connection between pore formation and cytotoxicity," PLoS One 7(1O):e47261.
Prangkio, P. et al. (Dec. 2011, e-published Aug. 26, 2011). "Self-assembled, cation-selective ion channels from an oligo(ethylene glycol) derivative of benzothiazole aniline," Biochim Biophys Acta 1808(12):2877-2885.
PubChem CID 13456094. 2-(2-(2-(2-Hydroxyethoxy)ethoxy)ethoxy)ethyl 4-methylbenzenesulfonate. Feb. 8, 2007. 12 pages.
PubChem CID 19609441. 2-(4'-Heptyloxyphenyl)benzothiazole. Dec. 5, 2007. 8 pages.
Slachta, A., PET imaging suggests major depression is a neurodegenerative disease, Care Delivery, Feb. 27, 2018, retrieved from the internet radiologybusiness.com/topics/care-delivery/pet-imaging-suggests-major-depression-neurodegenerative-disease on Feb. 16, 2021. 6 pages.
Song, J.M. et al. (Feb. 2014, e-published Dec. 6, 2013). "A tetra(ethylene glycol) derivative of benzothiazole aniline ameliorates dendritic spine density and cognitive function in a mouse model of Alzheimer's disease," Exp Neural 252:105-113.
Supplementary European Search Report and Search Opinion dated Jul. 19, 2019 for EP Application No. 17736233.2. 7 pages.
Trujillo-Estrada et al., "SPG302 Reverses Synaptic and Cognitive Deficits Without Altering Amyloid or Tau Pathology in a Transgenic Model of Alzheimer's Disease," Neurotherapeutics, 2021, vol. 18, pp. 2468-2483.
Wang et al., "Fascin inhibitor increases intratumoral dendritic cell activation and anti-cancer immunity," Cell Reports, 2021, vol. 35, 39 pages.
Wu, et al. Supporting Information—Triethylene glycol-modified iridium(iii) complexes for fluorescence imaging of Schistosoma japonicum. Journal of Materials Chemistry. Jan. 1, 2017; pp. 1-3.
Wu, et al. Triethylene glycol-modified iridium(iii) complexes for fluorescence imaging of Schistosoma japonicum. Journal of Materials Chemistry. Jan. 1, 2017; 5(25):4973-4980.
Yang, J. et al. (Jul. 26, 2002). "Catalytic oxidations of steroid substrates by artificial cytochrome p-450 enzymes," J Org Chem 67(15):5057-5067.
Zhao, X. et al. (Oct. 20, 2010). "Amyloid-β peptide is a substrate of the human 20S proteasome," ACS Chem Neurosci 1(10):655-660.
International Search Report & Written Opinion dated Aug. 16, 2022 for PCT/US2022/016936. 19 pages.
PubChem SID 438591027. Modify Date: Dec. 8, 2020. 5 pages.

* cited by examiner

METHODS OF TREATING SPINAL CORD INJURY OR DAMAGE

CROSS-REFERENCE TO RELATED APPLICATIONS

This application is a U.S. National Stage Application under 35 U.S.C. 371 of International Application No. PCT/US2022/016936, filed Feb. 18, 2022, which claims the benefit under 35 U.S.C. § 119(e) of U.S. Provisional Application No. 63/287,710, filed Dec. 9, 2021, and U.S. Provisional Application No. 63/152,174, filed Feb. 22, 2021, each of which is hereby incorporated by reference in its entirety.

FIELD

Provided herein are methods for treating spinal cord injury and promoting spinogenesis in patients who have suffered a spinal cord injury or damage.

BACKGROUND

Spinal cord injury (SCI) is a serious source of hospitalization, and many patients having such injuries require medium term or long term care. The average stay in hospital acute care for such patients is 11 days and rehabilitation stays are 31 days. Spinal cord injuries are also a source of significant morbidities. For example, 39.5% of spinal cord injured individuals are considered paraplegic and 59.9% are considered quadriplegic. Cost of care for such patients is substantial. Researchers have estimated that, as of 2019, 17,730 new SCI cases occur each year and between 249,000 and 363,000 people are currently living with SCI in the United States. Spinal cord injury may arise from damage or loss of neurons and the synaptic connections between them. Secondary conditions that may arise from spinal cord injury include diseases of the genitourinary system, disease of the skin, respiratory ailments, digestive ailments, circulatory ailments, and musculoskeletal diseases. Under some circumstances, rehospitalization may be required. Respiratory complications associated with SCI are an important cause of morbidity and mortality in both acute and chronic stages.

Spinal cord injury may also be accompanied by loss of neuronal health. Neuronal degeneration may arise as loss of synapses (junctions between two different neurons) and ultimately loss of neurons (neurodegeneration). Neurons within the spinal cord receive excitatory input from axons that use glutamate as a neurotransmitter, and the postsynaptic element can be a dendritic spine. Such connections are often damaged or lost in spinal cord injuries, leading to impairments in voluntary muscle control and autonomic functions. The development of novel methods to restore spine density following SCI could have important implications for treatment of a host of complications arising from spinal cord injury, and address the underlying damage to the spine.

The identification of a new cellular target for small molecules could lead to treatments for neuronal disorders and complications of injury to the spinal cord. Thus, small molecules that promote spine formation have potential use in ameliorating complications arising from SCI. However, there is a need for pharmaceutically acceptable compounds having such activity.

SUMMARY

Provided herein are methods for treating spinal cord injury or damage, or a complication thereof in patients who have suffered a spinal cord injury or damage.

In some embodiments, this disclosure provides a method for treating spinal cord injury or damage, or a complication thereof is provided, comprising contacting a compound as described herein.

In some embodiments, this disclosure provides a method of treating a spinal cord injury or damage, or a complication thereof, in a patient, comprising administering to a patient in need thereof a therapeutically effective amount of a compound of formula I or Ia:

I

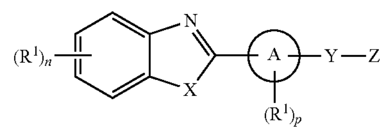

Ia

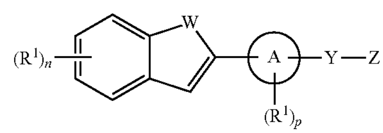

or a pharmaceutically acceptable salt, solvate, and/or an N-oxide thereof, wherein:

- subscripts n and p are independently selected from 0, 1, or 2;
- each $R^1$ is independently selected from the group consisting of hydrogen, halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro;
- A is an arylene or heteroarylene, having 1 to 4 heteroatoms;
- W is selected from the group consisting of —O—, —S—, —SO—, —S(O)$_2$—, and —NR$^2$—, wherein $R^2$ is selected from the group consisting of hydrogen, alkyl, substituted alkyl, aryl, substituted aryl, heteroaryl, substituted heteroaryl, heterocyclyl, and substituted heterocyclyl;
- X is selected from the group consisting of —O—, —S—, —SO—, —S(O)$_2$—, and —NR$^2$—, provided that when A is arylene, and Y is —S— or —NR$^2$—, then X is not —S—;
- Y is selected from the group consisting of —O—, —S—, —SO—, S(O)$_2$—, and —NR$^2$—; and
- Z is selected from the group consisting of —N(CH$_3$)$_2$ CH$_2$CH$_2$OC(O)CH$_3$ and —(CH$_2$CH(R$^3$)O)$_q$-T, wherein subscript q is an integer from 1 to 100, $R^3$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate.

In some embodiments, this disclosure provides a method of treating a spinal cord injury or damage, or a complication thereof, in a patient, comprising administering to a patient in need thereof a therapeutically effective amount of a compound of formula II:

II

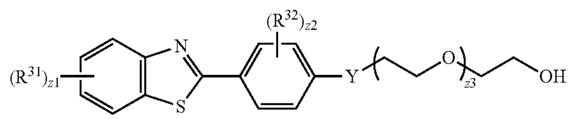

or a pharmaceutically acceptable salt, solvate, and/or an N-oxide thereof, wherein:

Y is $—NR^{33}—$ or —S—;

each $R^{31}$ is independently halogen, $—CX^{31}$, $—CHX^{31}$, $—CH_2X^{31}$, $—OCX^{31}_3$, $—OCHX^{31}_2$, $—OCH_2X^{31}$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—C(O)NHNH_2$, $—NHC(O)NH_2$, $—NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

each $R^{32}$ is independently halogen, $—CX^{32}_3$, $—CHX^{32}_2$, $—CH_2X^{32}$, $—OCX^{32}_3$, $—OCHX^{32}_2$, $—OCH_2X^{32}$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

$R^{33}$ is H, alkyl, or substituted alkyl;

each of $X^{31}$ and $X^{32}$ is independently halogen;

each of z1 and z2 is independently an integer from 0 to 4; and z3 is an integer from 1 to 12.

In some embodiments, the complication of spinal cord injury or damage is a respiratory complication, cardiovascular complication, hypotension, bradycardia, neurogenic shock, an autonomic dysreflexia, secondary immunodeficiency, syringomyelia, neuropathic joint arthropathy, Charcot joint arthropathy, loss of motor control, loss of sensory function, tetraplegia, paraplegia, loss of bladder control, spasm, loss of sexual function, numbness, loss of balance, deep vein thrombosis, spasticity, pain, neuropathic pain, syringomyelia, neurogenic heterotopic ossification, shock, bradyarrhythmias, hypotension, ectopic beats, abnormal temperature regulation, changes in sweat secretion, vasodilatation, thromboembolism, pressure ulcer, or heterotopic ossification, or a combination thereof.

DETAILED DESCRIPTION

Figure 1A:
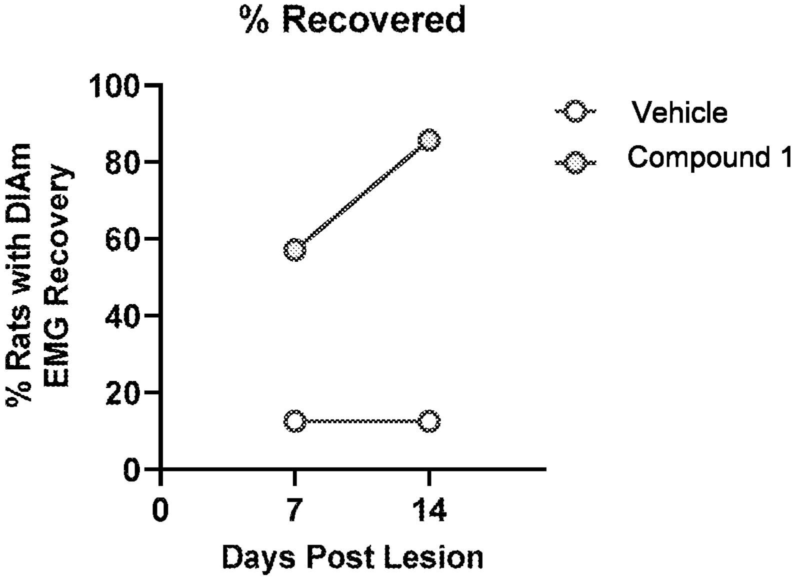
FIG. 1A illustrates enhancement of recovery from spinal cord injury in rats treated with Compound 1 of this disclosure as judged by diaphragm EMG and FIG. 1B illustrates magnitude of recovery rats treated with Compound 1 as compared with the vehicle (0.5% DMSO in phosphate buffered saline).

Generally the compounds and methods described herein provide for the administration of compounds that provide benefit in the treatment of spinal cord injury or damage, or a complication thereof. In some embodiments, the compositions and methods are useful for treating a complication arising from neuron damage incurred in spinal cord injury. Generally, the active ingredient or principal ingredient will include an agent, such as a compound, or a deuterated analog, pharmaceutically acceptable salt, solvate, prodrug, stereoisomer, or mixture of stereoisomers of a compound as described herein. The compound described herein may also be administered with one or more additional pharmaceutically active materials or in combination with one or more non-drug therapies.

I. Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A "pediatric patient" is a person less than 18 years of age. A "juvenile patient" is a person who has not reached physical maturity.

The term "spinogenesis" and the like refer, in the usual and customary sense, to development (e.g. growth and/or maturation) of dendritic spines in neurons. In some embodiments, the compounds provided herein promote spinogenesis without altering the normal distribution of spine morphologies. The promotion is relative to the absence of administration of the compound.

As used herein, the term "dendrite" refers to the branched extension of a neuron cell. Dendrites are typically responsible for receiving electrochemical signals transmitted from the axon of an adjacent neuron. The terms "dendritic spines" or "dendrite spines" refer to protoplasmic protuberances on a neuron cell (e.g., on a dendrite). In some embodiments, dendritic spines may be described as having a membranous neck which may be terminated with a capitulum (e.g., head). Dendritic spines are classified according to their shape: such as thin, stubby, or mushroom. Dendritic spine density refers to the total number of dendritic spines per unit length of a neuron cell. For example, the dendritic spine density may be given as the number of dendritic spines per micron.

The term "dendritic spine formation" and the like refer, in the usual and customary sense to processes which lead to an increased number of dendritic spines or increased development of dendritic spines. The term "dendritic spine morphology" and the like refer, in the usual and customary sense, to physical characterization of a dendritic spine (e.g., shape and structure). Improvement of dendritic spine morphology is a change in morphology (e.g., increase in length or increase in width) that results in increased functionality, such as may occur with, but not limited to, an increase in the number of synaptic contacts between neurons, an increase in the spine head volume and area of the associated post-synaptic density (PSD), a "maturation" of spines such that more are of the mushroom shape than thin shape, an better alignment of the PSD with pre-synaptic sites of glutamate release (i.e. "active zones"), an increase in the width of spine necks, and clustering of dendritic spines within a locality of dendritic membrane. As known in the art and disclosed herein, exemplary methods for such characterization include measurement of the dimensions (i.e., length and width) of dendritic spines. Accordingly, the term "improving dendritic spine morphology" generally refers to an increase in length, width, or both length and width of a dendritic spine.

"Binding" refers to at least two distinct species (e.g. chemical compounds including biomolecules, or cells) to becoming sufficiently proximal to react or interact thereby resulting in the formation of a complex. For example, the binding of two distinct species (e.g., a protein and a compound described herein) may result in the formation of a complex wherein the species are interacting via non-covalent or covalent bonds. In some embodiments, the resulting complex is formed when two distinct species (e.g., a protein and a compound described herein) interact via non-covalent bonds (e.g., electrostatic, van der Waals, or hydrophobic).

As defined herein, the term "activation," "activate," "activating" and the like in reference to a protein-activator (e.g. agonist) interaction means positively affecting (e.g. increasing) the activity or function of the protein relative to the activity or function of the protein in the absence of the activator (e.g. compound described herein).

As defined herein, the terms "inhibition," "inhibit," "inhibiting" and the like, are to be given their customary meanings to those of skill in the art. In reference to a protein-inhibitor (e.g. antagonist) interaction, the terms "inhibition," "inhibit," "inhibiting" mean negatively affecting (e.g. decreasing) the functional activity of the protein relative to the functional activity of the protein in the absence of the inhibitor.

A dash ("—") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy nitro, —$SO_3H$, substituted sulfonyl, substituted sulfonyloxy, and thiol.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxyl, heteroaryl, substituted heteroaryl, heteroaryloxy, substituted heteroaryloxy, heterocyclic, substituted heterocyclic, heterocyclyloxy, substituted heterocyclyloxy, nitro, $SO_3H$, substituted sulfonyl, substituted sulfonyloxy and thiol and with the proviso that any hydroxyl or thiol substitution is not attached to a vinyl (unsaturated) carbon atom.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—. Acyl includes the "acetyl" group $CH_3C(O)$—.

"Acylamino" refers to the groups —$NR^{47}C(O)$alkyl, —$NR^{47}C(O)$substituted alkyl, —$NR^{47}C(O)$cycloalkyl, —$NR^{47}C(O)$substituted cycloalkyl, —$NR^{47}C(O)$cycloalkenyl, —$NR^{47}C(O)$substituted cycloalkenyl, —$NR^{47}C(O)$alkenyl, —$NR^{47}C(O)$substituted alkenyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic, wherein $R^{47}$ is hydrogen or alkyl.

"Acyloxy" refers to the groups alkyl-C(O)O—, substituted alkyl-C(O)O—, alkenyl-C(O)O—, substituted alkenyl-C(O)O, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—.

"Alkynyl" refers to an unbranched or branched hydrocarbon group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having at least one carbon-carbon triple bond and a carbon-carbon double bond.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy. "Substituted alkoxy" refers to the group —O-(substituted alkyl) wherein substituted alkyl is defined herein.

"Haloalkoxy" refers to an alkoxy group as defined above, wherein one or more hydrogen atoms are replaced by a halogen.

"Alkylthio" refers to the group "alkyl-S—".

"Amido" refers to both a "C-amido" group which refers to the group —C(O)$NR^yR^z$ and an "N-amido" group which refers to the group —$NR^y$C(O)$R^z$, wherein $R^y$ and $R^z$ are independently selected from the group consisting of hydrogen, alkyl, aryl, haloalkyl, or heteroaryl; each of which may be optionally substituted.

"Amino" refers to the group —$NH_2$. "Substituted amino" refers to the group —$NR^{48}R^{49}$, wherein $R^{48}$ and $R^{49}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic, and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen.

"Aminocarbonyl" refers to the group —C(O)$NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group. "Aminocarbonylamino" refers to the group —$NR^{47}$C(O)$NR^{50}R^{51}$, wherein $R^{47}$ is hydrogen or alkyl; $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic; and, wherein $R^{50}$ and $R^{51}$ are optionally joined together with the nitrogen bound thereto to form a heterocyclic or substituted heterocyclic group.

"Aminocarbonyloxy" refers to the group —O—C(O)$NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonyl" refers to the group —$SO_2NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonyloxy" refers to the group —O—$SO_2NR^{50}R^{51}$ wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonylamino" refers to the group —$NR^{47}SO_2NR^{50}R^{51}$, wherein $R^{47}$ is hydrogen or alkyl; $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic; and, wherein $R^{50}$ and $R^{51}$ are optionally joined together with the nitrogen bound thereto to form a heterocyclic or substituted heterocyclic group.

"Amidino" refers to the group —C(=$NR^{52}$)$NR^{50}R^{51}$, wherein $R^{50}$, $R^{51}$, and $R^{52}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aryl" or "Ar" refers to a monovalent aromatic carbocyclic group of from 6 to 14 carbon atoms having a single ring (e.g., phenyl) or multiple condensed rings (e.g., naphthyl or anthryl). The condensed rings may or may not be aromatic (e.g., 2-benzoxazolinone, 2H-1,4-benzoxazin-3(4H)-one-7-yl, and the like), provided that the point of attachment is at an aromatic carbon atom. Preferred aryl groups include phenyl and naphthyl. "Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, $SO_3H$, substituted sulfonyl, substituted sulfonyloxy, and thiol.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Aryloxy" refers to the group —O-aryl, wherein aryl is as defined herein. Exemplary aryloxy groups include phenoxy and naphthoxy. "Substituted aryloxy" refers to the group —O-(substituted aryl).

"Carbonyl" refers to the divalent group —C(O)— (i.e., —C(═O)—).

"Aralkyl" refers to an aryl group pendant to an alkyl group. Examples of aralkyl groups include benzyl, phenethyl, and 3-naphthylpropyl.

"Carbamoyl" refers to both an "O-carbamoyl" group which refers to the group —O—C(O)$NR^yR^z$ and an "N-carbamoyl" group which refers to the group —$NR^y$C(O)$OR^z$, wherein $R^y$ and $R^z$ are independently selected from the group consisting of hydrogen, alkyl, aryl, haloalkyl, or heteroaryl; each of which may be optionally substituted.

"Carboxyl" or "carboxy" refers to —COOH, or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-aryl, —C(O)(O)-substituted aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic. "(Carboxyl ester)amino" refers to the group —$NR^{47}$C(O)(O)-alkyl, —$NR^{47}$C(O)(O)-substituted alkyl, —$NR^{47}$C(O)O-alkenyl, —$NR^{47}$C(O)(O)-substituted alkenyl, —$NR^{47}$C(O)(O)-aryl, —$NR^{47}$C(O)(O)-substituted-aryl, —$NR^{47}$C(O)(O)-cycloalkyl, —$NR^{47}$C(O)(O)-substituted cycloalkyl, —$NR^{47}$C(O)(O)-cycloalkenyl, —$NR^{47}$C(O)(O)-substituted cycloalkenyl, —$NR^{47}$C(O)(O)-heteroaryl, —$NR^{47}$C(O)(O)-substituted heteroaryl, —$NR^{47}$C(O)(O)-heterocyclic, and —$NR^{47}$C(O)(O)-substituted heterocyclic. "(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic.

"Cyano" refers to the group —CN.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. "Cycloalkenyl" refers to cycloalkyl groups which are partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl. Cycloalkyl and cycloalkenyl groups can be substituted or unsubstituted. "Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, $SO_3H$, substituted sulfonyl, substituted sulfonyloxy, and thiol.

"Cycloalkyloxy" refers to —O-cycloalkyl. "Substituted cycloalkyloxy" refers to —O-(substituted cycloalkyl). "Cycloalkenyloxy" refers to —O-cycloalkenyl. "Substituted cycloalkenyloxy" refers to —O-(substituted cycloalkenyl).

"Guanidino" refers to the group —NHC(═NH)$NH_2$.

"Hydroxy" or "hydroxyl" refers to the group —OH.

"Imino" refers to a group —C(NR)R, wherein each R is independently alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —$S(O)_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, which may or may not contain a heteroatom, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, benzofuran, indolizine or benzothiene. The heteroaryl groups can be fused to non-aromatic ring systems, which may or may not contain a heteroatom, provided that the point of attachment is through an atom of the aromatic heteroaryl group. For example, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thiazolyl, and furanyl. Other heteroaryl groups include heteroaryl rings linked by a bond, such as bipyridine. Heteroaryl groups can be substituted or unsubstituted. "Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroarylene" refers to a divalent heteroaryl. "Substituted heteroarylene" refers to a heteroarylene having from 1 to 5, preferably 1 to 3, or more preferably 1 to 2 substituents as defined for heteroaryl groups.

"Heteroaryloxy" refers to —O-heteroaryl. "Substituted heteroaryloxy" refers to the group —O-(substituted heteroaryl).

"Heterocycle" or "heterocyclic" or "heterocycloalkyl" or "heterocyclyl" refers to a saturated, or partially saturated, ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties. Heterocycloalkyl groups can be unsubstituted or substituted. For example, heterocycloalkyl groups can be substituted with $C_{1-6}$ alkyl, oxo (═O), nitro (—$NO_2$), or sulfonyl (—$S(O)_2$—), among many others. "Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocyclyl. "Substituted heterocyclyloxy" refers to the group —O-(substituted heterocyclyl).

"Oxo" refers to the group (═O) or (O).

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

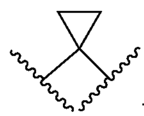

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl. "Substituted sulfonyl" refers to the group —$SO_2$-alkyl, —$SO_2$-substituted alkyl, —$SO_2$-alkenyl, —$SO_2$ -substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$ -heteroaryl, —$SO_2$-substituted heteroaryl, —$SO_2$-heterocyclic, —$SO_2$-substituted heterocyclic. Substituted sulfonyl includes groups such as methyl-$SO_2$—, phenyl-$SO_2$—, and 4-methylphenyl-$SO_2$—. "Substituted sulfonyloxy" refers to the group —$OSO_2$-alkyl, —$OSO_2$-substituted alkyl, —$OSO_2$-alkenyl, —$OSO_2$-substituted alkenyl, —$OSO_2$-cycloalkyl, —$OSO_2$-substituted cylcoalkyl, —$OSO_2$-cycloalkenyl, —$OSO_2$-substituted cylcoalkenyl, —$OSO_2$-aryl, —$OSO_2$-substituted aryl, —$OSO_2$-heteroaryl, —$OSO_2$-substituted heteroaryl, —$OSO_2$-heterocyclic, and —$OSO_2$-substituted heterocyclic.

"Alkylsulfonyl" refers to the group —$S(O)_2R$, where R is alkyl.

"Alkylsulfinyl" refers to the group —S(O)R, where R is alkyl.

As used herein, the term "saccharide" refers to a sugar, such as a monosaccharide, a disaccharide, an oligosaccharide or a polysaccharide. Monosaccharides include, but are not limited to, glucose, ribose and fructose. Disaccharides include, but are not limited to, sucrose and lactose. Oligosaccharides refers to 2 to 10 sugars linked together preferably through an alpha linkage. Examples of oligosaccharides include maltose, lactose, sucrose, and the like. Polysaccharides include, but are not limited to, cellulose, hemicellulose and lignocellulose or starch. Saccharides or sugars useful in the present invention include any and all naturally occurring sugars, such as, but not limited to, glucose, glucuronic acid, iduronic acid, galactose, fucose, glucosamine, N-acetylglucosamine, fructose, sialic acid, including aldol and pyranose forms thereof, as well as D and L isomers thereof.

"Thiocyanate" refers to the group —SCN.

"Thioxo" or "thione" refer to the group (═S) or (S).

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

The groups defined above can optionally be substituted by any suitable number and type of substituents. Representative substituents include, but are not limited to, alkyl, alkenyl, alkynyl, aryl, cycloalkyl, heteroalkyl, heteroaryl, heterocycloalkyl, halogen, haloalkyl, haloalkoxy, —OR', ═O, —OC(O)R', —(O)R', —$O_2$R', —ONR'R", —OC(O)NR'R", ═NR', ═N—OR', —NR'R", —NR"C(O)R', —NR'—(O)NR"R"', —NR"C(O)OR', —NH—($NH_2$)═NH, —NR'C($NH_2$)═NH, —NH—($NH_2$)═NR', —SR', —S(O)R', —$S(O)_2$R', —$S(O)_2$NR'R", —NR'$S(O)_2$R", —$N_3$ and —$NO_2$. R', R" and R"' each independently refer to hydrogen, unsubstituted alkyl, such as unsubstituted $C_{1-6}$ alkyl. Alternatively, R' and R", or R" and R"', when attached to the same nitrogen, are combined with the nitrogen to which they are attached to form a heterocycloalkyl or heteroaryl ring, as defined above.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. In other words, each of the above definitions is constrained by a limitation that, for example, substituted aryl groups are limited to -substituted aryl-(substituted aryl)-substituted aryl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. The term "optionally substituted" with reference to a group is intended to be construed as describing the unsubstituted group and the group substituted by the indicated or defined substituent(s).

A protecting group may be any known in the art, for example, as described in Peter G. M. Wuts and Theodora W. Greene, Greene's protective groups in organic synthesis (Wiley-Interscience, 2007).

Some compounds exist as tautomers. For example, amide containing compounds may exist in equilibrium with imidic acid tautomers. Regardless of which tautomer is shown, and regardless of the nature of the equilibrium among tautomers, the compounds are understood by one of ordinary skill in the art to comprise all tautomers.

Any formula or structure given herein is also intended to represent isotopically labeled forms of the compounds as well as unlabeled forms. Isotopically labeled compounds have structures depicted by the formulas given herein except that one or more atoms are replaced by an isotope having the indicated atomic mass or mass number. Examples of isotopes that can be incorporated into compounds of the disclosure, or counter-ions thereto, include isotopes of hydrogen, carbon, nitrogen, oxygen, phosphorous, fluorine and chlorine, such as, but not limited to $^2$H (deuterium, D), $^3$H (tritium), $^{11}$C, $^{13}$C , $^{14}$C , $^{15}$N , $^{18}$F , $^{31}$P, $^{32}$P, $^{35}$S, $^{36}$Cl and $^{125}$I. Various isotopically labeled compounds are possible under the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds, and counter-ions thereto, in which from 1 to n hydrogens attached to a carbon atom is/are replaced by deuterium, in which n is the number of hydrogens in the molecule. Such compounds may exhibit increased resistance to metabolism and thus may be useful for increasing the half-life of a compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent enrichment of deuterium above a naturally occurring level at the indicated position.

Compounds described herein may be present as a salt, such as a pharmaceutically acceptable salt. Compounds are capable of forming salts such as acid and/or base salts. Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. Salts of compounds described herein can be prepared according to procedures described herein and as known in the art.

The term "pharmaceutically acceptable salt" of a given compound, refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, isobutyric acid, suberic acid, lactic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri- arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like. Methods of preparing a salt also include mixing a compound by redox reaction with an active metal, or by exchange of ions, for example, due to differing solubility of salts.

The term "substituted" means that any one or more hydrogen atoms on the designated atom or group is replaced with one or more substituents other than hydrogen, provided that the designated atom's normal valence is not exceeded. If not specified, the one or more substituents include, but are not limited to, alkyl, alkenyl, alkynyl, alkoxy, acyl, amino, amido, aryl, —$N_3$, carbamoyl, carboxyl, carboxyl ester, —CN, halo, haloalkyl, haloalkoxy, heteroalkyl, heteroaryl, heterocyclyl, —OH, imino, oxo, —$NO_2$, alkylsulfinyl, —$SO_3H$, alkylsulfonyl, thiocyanate, —SH, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorine atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

A "solvate" is a solid form of a compound in which solvent molecules are incorporated. A solvate is formed by the interaction of a solvent and a compound. A hydrate is a solvate in which the solvent is water. Solvates of salts of compounds described herein are also provided.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" provides a beneficial or desired result, e.g., an improvement in one or more clinical indicia of a disorder. Beneficial or desired results may include one or more of the following: decreasing or ameliorating one or more symptoms of the disorder, and/or diminishing the extent of the disorder; (e.g., stabilizing the disorder, preventing or delaying the worsening or progression of the disorder); providing partial or total remission of the disorder; enhancing effect of another medication; increasing the quality of life; and/or prolonging survival in a population of patients.

"Prevention" or "preventing" means blocking development of a disorder, or symptoms thereof. Compounds may, in some embodiments, be administered to a subject (including a human) who is at risk of or has a family history of the disorder. Prevention may comprise delay in reaching predefined disease milestones or reduction in appearance or progression of a marker.

"Subject" refers to an animal, such as a mammal, e.g. a human that may benefit from administration of a compound described herein. The methods described herein may be useful in human therapy and/or veterinary applications. In some embodiments, the subject is a mammal. In some embodiments, the subject is a human. When the subject is a human person, the subject may be referred to as a "patient."

The term "therapeutically effective amount" or "effective amount" of a compound described herein means an amount sufficient to effect treatment when administered to a subject, to provide a benefit as described herein. For example, a therapeutically effective amount may be an amount sufficient to decrease a symptom of a mood disorder. The therapeutically effective amount may vary depending on the subject, the disorder being treated, the weight and age of the subject, the severity of the disorder, and the manner of administering, which can readily be determined by a medical practitioner.

The term "refractory" means that a subject having a mood disorder has previously been resistant to treatment of the disorder. For example, one or more symptoms of the mood disorder persisted following treatment. In some embodiments, the subject is refractory to treatment with an antidepressant as described herein.

The term "marker" means a characteristic of a subject that indicates a risk for developing a disorder. For example, a marker may be a genetic indicator associated with a disorder; a marker may be a personal history of the disorder; a marker may be a family history, e.g., a genetic relative or relatives having had the disorder or a related disorder; or a marker may be a physiological indicator such as a test result.

Treatment Methods and Uses

Described herein are methods for the treatment of a spinal cord injury or damage, or a complication thereof, by administering to a patient an effective amount of a compound described herein. The methods described herein may also provide for treatment with reduced side effects, and/or for treatment of subjects who are nonresponsive or refractory to a conventional treatment.

Spinal Cord Injury, Complications Thereof, and Treatment Thereof

In further embodiments, the compositions and methods are provided for alleviating, reducing, or reversing spinal cord injury or damage, or a complication thereof. In further embodiments, the compositions and methods are provided for alleviating, reducing, or reversing a complication secondary to a spinal cord injury or damage. The complication may be any complication described herein.

Spinal cord injury occurs when damage is incurred at the vertebrae, ligaments or disks of the spinal column or to the spinal cord itself. Injury to the cauda equina is usually included in the definition, while other isolated injuries to nerve roots are excluded. Medical practitioners have the knowledge to diagnose and treat spinal cord injuries (SCI). The SCI may be any known in the art, for example, those arising from impact, incision, contusion, puncture, blunt trauma, compression, stretching, tearing, bone fracture, degeneration due to infection or disease, autoimmunity, or chemical damage. The SCI may be incomplete or complete. The SCI may be cervical, thoracic, lumbar or sacral. The SCI may comprise a spinal concussion. The spinal cord may suffer more than one category of injury or damage.

The SCI may be incomplete or complete. There are three common types of incomplete SCIs: anterior cord syndrome, central cord syndrome, and Brown-Sequard syndrome. A complete SCI may result in tetrapledia, paraplegia, or triplegia. SCIs may be graded according to the American Spinal Injury Association (ASIA) grading scale, which describes the severity of the injury. The scale is graded as follows:

ASIA A: injury is complete spinal cord injury with no sensory or motor function preserved.

ASIA B: a sensory incomplete injury with complete motor function loss.

ASIA C: a motor incomplete injury, where there is some movement, but less than half the muscle groups are anti-gravity (can lift up against the force of gravity with a full range of motion).

ASIA D: a motor incomplete injury with more than half of the muscle groups are anti-gravity.

ASIA E: normal.

Spinal cord injury (SCI) may be accompanied by one or more of a number of acute complications. Along with motor and sensory deficits, instabilities of the cardiovascular, thermoregulatory and broncho-pulmonary system are common after an SCI. Disturbances of the urinary and gastrointestinal systems are typical as well as sexual dysfunction. Frequent complications of cervical and high thoracic SCI are neurogenic shock, bradyarrhythmias, hypotension, ectopic beats, abnormal temperature control and disturbance of sweating, vasodilatation and autonomic dysreflexia. Autonomic dysreflexia is an abrupt, uncontrolled sympathetic response, elicited by stimuli below the level of injury. The symptoms may be mild like skin rash or slight headache, but can cause severe hypertension, cerebral hemorrhage and death. Frequent complications in the acute phase of are bradyarrhythmias and hypotension. Other complications are instability of temperature (hypothermia and hyperthermia), pain, spasticity and autonomic dysreflexia (AD). AD is associated with an abrupt, uncontrolled sympathetic response, elicited by stimuli below the level of injury, and it can cause severe hypertension, cerebral hemorrhage and death. Ischemia and edema may worsen the injury during the first few hours after an injury. The complication may be thromboembolism, pressure ulcer, or heterotopic ossification.

The complication may be a respiratory complication. Disturbance of respiratory function are frequent in tetraplegia and a primary cause of both short and long-term morbidity and mortality is pulmonary complications. Due to physical inactivity and altered hemostasis, patients with SCI have a higher risk of venous thromboembolism and pressure ulcers. Spasticity and pain are frequent complications. The psychological stress associated with SCI may lead to anxiety and depression. Complications during the acute phase are important because they may be life threatening and/ or may lead to prolonged rehabilitation.

The early acute phase is generally defined to be 2-48 h after the injury, the subacute phase from 2 days to 2 weeks, and the intermediate phase from 2 weeks to 6 months. The clinically acute phase is usually defined as the first 4-5 weeks after the injury. Surgery may be indicated within a few hours to a few days following the SCI.

An acute traumatic SCI typically starts with an abrupt, injury to the spine leading to fractures or dislocations of vertebrae. Displaced bone fragments and disc material causes the immediate injury leading to damage of axons and broken neural cell membranes. Ruptured blood vessels may cause bleeding in the spinal cord, and thereby increase the damage during the subsequent hours. Several mechanisms may contribute to the total injury of the spinal cord tissue.

Respiratory complications include diaphragm motor unit dysfunction, diaphragm muscle pathology, phrenic motor neuron pathology, loss of phrenic motor neurons, loss of phrenic neuron spines (including those with classic thin, stubby and mushroom shapes, but also synapses that innervate the dendritic shaft directly), loss of transdiaphragmatic pressure, loss of diaphragm muscle force generation, dysphagia, atelectasis, pneumonia, and respiratory failure.

Neurogenic shock may arise due to severe hypotension and bradycardia in cervical injuries due to drop in blood pressure in relation to an acute SCI. Hypotension may be defined as systolic blood pressure<90 mmHg in supine position, and due to low intravascular volume (e.g., blood loss, dehydration). Because of an intact parasympathetic influence via the vagal nerve and a loss of sympathetic tone due to disruption in supraspinal control, neurogenic shock develops as a result of imbalance of the autonomic control. Depending on the severity of the SCI, prolonged and severe hypotension, requiring vasopressive therapy may last up to 5 weeks after injury. Some studies put the percentages of neurogenic shock was 19.3% of cervical injuries. In patients having thoracic and lumbar injuries the incidence has been measured at 7.0% and 3.0%, respectively.

Injuries to the autonomic nervous system are the cause of many of the cardiovascular complications following an SCI. Cardiovascular dysfunction in patients with cervical and high thoracic SCI may be life-threatening and may exacerbate the neurological impairment due to the spinal cord injury. Patients have higher morbidity and mortality as a result of the autonomic dysfunction. One study found that SCI is associated with an increased odds of heart disease and stroke compared to able body.

In the acute phase many irregularities of the cardiac rhythm may occur; sinus bradycardia and bradyarrhythmias (14%-77%) including escape rhythm, supraventricular ectopic beats (19%), ventricular ectopic beats (18%-27%), orthostatic hypotension (33%-74%), increased vasovagal reflex, vasodilatation and stasis. One study found that orthostatic hypotension persisted during the first month following SCI in 74% of cervical and 20% of upper thoracic motor complete SCI patients. Following cervical injuries both sinus bradycardia and arterial hypotension frequently arise. Bradycardia is reported in 64% to 77% of cervical SCI. Studies have found a peak in incidence four days post-injury, then a gradual decline in incidence. Arterial hypotension is reported in 68% of patients with motor complete cervical SCI (ASIA A and B) who develop bradycardia. Of these will 35% require vasopressors, and 16% will have a cardiac arrest. In the acute phase arterial hypotension in the acute phase can be misunderstood as loss of volume. This may lead to over hydration in the acute phase.

Common autonomic disturbances (AD) after 4 to 5 weeks post-injury are autonomic dysreflexia, orthostatic hypotension (also in sitting position), reduced cardiovascular reflexes (which regulate blood pressure, blood volume and body temperature) and the absence of cardiac pain. The prevalence of autonomic dysreflexia in patients with SCI with injury above Th6 is 48%-90%. One study found an incidence of early autonomic disturbances of 5.2% in a population of acute SCI, the earliest episode of AD occurred on the 4th post-injury day. Patients with cervical or thoracic injuries above Th4 may have disrupted the sympathetic afferent fibers including cardiac pain fibers; their sensation of ischemic cardiac pain may be changed (referred pain) or absent. Secondary cardiac changes in patients with tetraplegia, are loss of muscle mass in the left ventricle (due to physiological adaptation to reduced myocardial load) and pseudo infarction—a rise in Troponin with or without ECG changes An acute injury above the sixth thoracic (Th6) vertebra disturbs the descending pathways to neurons of the sympathetic trunk (in the intermediolateral cell column) from the first thoracic (Th1) to the second lumbar (L2) vertebrae. Complications that arise may include abolished supraspinal control of the sympathetic nervous system, and lack of inhibition of the parasympathetic nervous system resulting in an increased sympathetic activity below the injury level. Along with motor and sensory deficits, instabilities of the cardiovascular, thermoregulatory and broncho-pulmonary system are common after a SCI. Disturbances of the urinary and gastrointestinal systems are typical as well as sexual dysfunction. Patients with injury below Th6 will have intact sympathetic and parasympathetic control of the heart and lungs. Thus, the responses from the organ systems will differ between patients with tetraplegia and patients with paraplegia.

Abnormal temperature regulation may include poikilothermia—an inability to maintain a constant core temperature irrespective of the ambient temperature. Changes in sweat secretion often occur after SCI, and excessive sweating (hyperhidrosis), absence of sweating (anhidrosis) and diminished sweating (hypohidrosis) may all occur.

In some embodiments, the complication of spinal cord injury is a respiratory complication, cardiovascular complication, hypotension, bradycardia, neurogenic shock, an autonomic dysreflexia, secondary immunodeficiency, syringomyelia, neuropathic joint arthropathy, Charcot joint arthropathy, loss of motor control, loss of sensory function, tetraplegia, paraplegia, loss of bladder control, spasm, loss of sexual function, numbness, loss of balance, autonomic dysreflexia, deep vein thrombosis, spasticity, pain, neuropathic pain, syringomyelia, neurogenic heterotopic ossification, shock, bradyarrhythmias, hypotension, ectopic beats, abnormal temperature regulation, changes in sweat secretion, vasodilatation, autonomic dysreflexia, thromboembolism, pressure ulcer, or heterotopic ossification, or a combination thereof.

In further embodiments, the compositions and methods are provided for alleviating, reducing, or reversing a symptom of a spinal cord injury or damage, or a complication thereof. The symptom may be any symptom described herein.

Dendritic Spines

The role of spine density in the progress of SCI is not completely understood. Thus, the development of novel methods to increase spine density could have important implications for treatment of spinal cord injury or damage, and secondary conditions relating to SCI.

In some embodiments, a method provided herein comprises administering to the subject an effective amount of a compound described herein, whereby spinogenesis is promoted. Spinogenesis may be observed as an increase in the average number of spines per neuron, or a unit length of a neuron, which may be referred to as an increase in dendritic spine density. Spinogenesis may be observed as an improvement in dendritic spine morphology. For example, an improvement in dendritic spine morphology may be observed as an increase in average size of spine heads. Spinogenesis may be observed as an improvement in dendritic spine size, spine plasticity, spine motility, spine density and/or synaptic function. Spinogenesis may be observed as an increase in local spatial average of membrane potential. Spinogenesis may be observed as an increase in postsynaptic concentration (e.g., volume-averaged) of Ca2+. In some embodiments, a compound described herein, or a pharmaceutically acceptable salt thereof, increases the dendritic spine density relative to that observed at the time that treatment is initiated. In some embodiments, the increase in dendritic spine density results in a reduction in symptoms of a spinal cord injury or damage, or a complication thereof, in a subject or patient.

Fascin is an important actin cross-linker that has no amino-acid sequence homology with other actin-binding proteins. Three forms of fascin are found in vertebrates: fascin 1, widely found in the nervous system and elsewhere; fascin 2 found in the retinal photoreceptor cells; and fascin 3, which is only found in the testes. In some embodiments, a fascin is human fascin 1. Fascin has a molecular mass of 55 kDa, functions as a monomeric entity, and cross-links actin filaments into straight, compact and rigid bundles, to impart mechanical stiffness to actin bundles. It is believed that fascin holds parallel actin filaments together to form filopodia on the order of 60-200 nm in diameter.

During neuron development, it is believed that long bundles of f-actin push out the membrane of the neuron to form structures such as axons, dendrites, filopodia and lamellipodia. Fascin is thought to be involved in cytoskeletal reorganization of nascent dendritic protrusions. Thus, actin bundling by fascin is generally believed to be required for the formation and extension of axons and dendrites. Surprisingly, the present results indicate that inhibiting the activity of fascin, either its' ability to bundle actin or to bind to other protein factors with which it may have mutual regulatory interactions with, promotes the formation of dendritic spines, protrusions of the cytoplasmic membrane of dendrites.

Dendritic spines are specialized protrusions responsible for receiving synaptic inputs, providing an important function in communication between neurons. The morphology of dendritic spines and their overall density correlates with synaptic function. Cellular changes in neurons may contribute to pathogenesis of a neuronal disease. For example, an aberrant level (e.g., reduction) in dendritic spine density may contribute to the pathogenesis of the neuronal disease. Consequently, alteration or misregulation of dendritic spines is believed to influence synaptic function and play a major role in various neurological and psychiatric disorders. Therefore, treatment strategies that target the initial synaptic loss, rather than late stage disease intervention, may provide a better prognosis for the treatment of some neuronal disorders.

In some embodiments, the average dendritic spine density, relative to the time that treatment with a compound described herein, or a pharmaceutically acceptable salt thereof, is initiated, increases by at least about 5%, 10%, 15%, 20%, 25%, 30%, 35%, 40%, 45%, 50%, 60%, 70%, 80%, 90%, or 100% or any range between any two of the numbers, end points inclusive. In some embodiments, the dendritic spine density, relative to the time that treatment with a compound described herein, or a pharmaceutically acceptable salt thereof, is initiated, increases by about 10% to about 50%. In some embodiments, the dendritic spine density, relative to the time that treatment with a compound described herein, or a pharmaceutically acceptable salt thereof, is initiated, increases by about 10% to about 40%. In some embodiments, the dendritic spine density, relative to the time that treatment with a compound described herein, or a pharmaceutically acceptable salt thereof, is initiated, increases by about 10% to about 30%. In some embodiments, the duration of treatment with a compound described herein, or a pharmaceutically acceptable salt thereof, is 15 minutes, 30 minutes, 1 hour, 2 hours, 4 hours, 8 hours, 1 day, 3 days, 5 days, 7 days, 14 days, 28 days, 90 days, 180 days, or 365 days. In some embodiments, the administration is not continuous, and is, for example, conducted in discrete administrations on the specified days.

In some embodiments, the method increases spine density through promoting the formation of new spines. In some embodiments, the method increases the average spine density by at least about 5%, 10%, 15%, 20%, 25%, 30%, 35%, 40%, 45%, 50%, 60%, 70%, 80%, 90%, or 100%, or any range between any two of the numbers, end points inclusive, relative to a control (e.g., the spine density in the absence of the compound). In some embodiments, the method increases the spine density about 10% to about 50% relative to a control (e.g., the spine density in the absence of the compound). In some embodiments, the method increases the spine density about 10% to about 40% relative to a control (e.g., the spine density in the absence of the compound). In some embodiments, the method increases the spine density about 10% to about 30% relative to a control (e.g., the spine density in the absence of the compound).

In some embodiments, the method increases the average number of spines per neuron, relative to the time that treatment with a compound described herein, or a pharmaceutically acceptable salt thereof, is initiated. In some embodiments, average number spines per unit length of a neuron increases by at least about 10, 20, 30, 40, 50, 60, 70, 80, 90, 100, 200, 300, 400, 500, 600, 700, 800, 900, or about 1000 more, or any range between any two of the numbers, end points inclusive. In some embodiments, the time is 1 hour, 2 hours, 4 hours, 8 hours, 1 day, 3 days, 5 days, 7 days, 14 days, 28 days, 90 days, 180 days, or 365 days.

In some embodiments, the time to realize a change in spine density or spine morphology described herein, for example, average dendritic spine density, average spine density, average neuron length, or average number of spines per neuron, is 1 hour, 2 hours, 4 hours, 8 hours, 1 day, 3 days, 5 days, 7 days, 14 days, 28 days, 90 days, 180 days, or 365 days. In some embodiments, the time to realize a change in spine density or spine morphology described herein, for example, average dendritic spine density, average spine density, average neuron length, or average number of spines per neuron, is 1 hour, 2 hours, 4 hours, 8 hours, or 1 day.

In some embodiments, the compounds are useful in the treatment of neuronal diseases and disorders arising from spinal cord injury or damage, or a complication thereof. A neuronal disease is a disease or condition in which the function of a subject's nervous system becomes impaired. The neuronal disease or disorder may be a neurological disease or disorder. The neuronal disease or disorder may be associated with a neurodegenerative disease or disorder, for example, ALS. The neuronal disease or disorder, or the neurodegenerative disease or disorder, may be acute (e.g., arising at the time of injury or damage to the spinal cord), or may arise at a time subsequent to the injury or damage to the spinal cord. In some embodiments, the patient has a condition associated with neuronal damage, such as, for example, Chiari malformation, radiculopathy, hydrocephalus, neuropathy due to infections, for example, any of which may be associated with spinal cord injury or damage.

In an aspect is provided a method of treating spinal cord injury or damage, or a complication thereof, in a patient in need thereof, the method comprising administering a therapeutically effective amount of a compound described herein, or a pharmaceutically acceptable salt thereof, to the patient. In some embodiments, the complication is a complication described herein.

In some embodiments, the neuronal disease includes a neuronal impairment. A neuronal impairment may include atrophy or other decrease in the effective functioning of the neuron.

In some embodiments, the neuronal disease is associated with abnormal dendritic spine morphology, spine size, spine plasticity, spine motility, spine density and/or abnormal synaptic function. In some embodiments, the neuronal disease is associated with an abnormal (e.g., reduced) level of dendritic spine density.

Examples of diseases and disorders that may be treated with a compound or method described herein include Alexander's disease, Alper's disease, Alzheimer's disease, depression, perinatal asphyxia, Parkinson's disease dementia ("PD dementia"), amyotrophic lateral sclerosis (ALS), ataxia telangiectasia, Batten disease (also known as Spielmeyer-Vogt-Sjogren-Batten disease), spongiform encephalopathy (e.g., bovine spongiform encephalopathy (mad cow disease), Kuru, Creutzfeldt-Jakob disease, fatal familial insomnia, Canavan disease, Cockayne syndrome, corticobasal degeneration, fragile X syndrome, frontotemporal dementia, Gerstmann-Straussler-Scheinker syndrome, Huntington's disease, HIV-associated dementia, Kennedy's disease, Krabbe's disease, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff s disease, Schilder's disease, subacute combined degeneration of spinal cord secondary to pernicious anaemia, schizophrenia, spinocerebellar ataxia (multiple types with varying characteristics), spinal muscular atrophy, Steele-Richardson-Olszewski disease, Tabes dorsalis, drug-induced Parkinsonism, progressive supranuclear palsy, corticobasal degeneration, multiple system atrophy, idiopathic Parkinson's disease, autosomal dominant Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or mitochondrial Parkinson's disease. In some embodiments, the neuronal disease is Alzheimer's disease, Parkinson's disease, Parkinson's dementia, autism, stroke, post-traumatic stress disorder (PTSD), traumatic brain disorder (TBD), chronic traumatic encephalopathy (CTE), schizophrenia, dementia (e.g., general dementia), attention-deficit/hyperactivity disorder (ADHD), amyotrophic lateral sclerosis (ALS), frontotemporal lobar degeneration (FTLD) (e.g., FTLD-tau, FTLD-TDP, or FTLD-FUS), memory loss (e.g., age-related memory loss), hypertensive encephalopathy, or chronic stress. In some embodiments, the condition treated is amyotrophic lateral sclerosis (ALS). In some embodiments, the spinal cord damage is a result of amyotrophic lateral sclerosis (ALS). In some embodiments, the patient has ALS.

In some embodiments, the subject has been found to suffer abnormal dendritic spine morphology, spine size, spine plasticity, spine motility, spine density and/or abnormal synaptic function. In some embodiments, the complication arising from SCI is associated with an abnormal (e.g., reduced) level of dendritic spine density. The abnormal spine density may be characterized as a reduction in number, change in morphology, change in proportion or population of particular morphologies of dendritic spines, or reduction in spine density.

In some embodiments, a method for promoting spinogenesis in a patient having spinal cord injury or damage is provided, comprising administering to the patient a compound described herein, or a pharmaceutically acceptable salt thereof. In some embodiments, a compound for use in the manufacture of a medicament for the treatment of a spinal cord injury or damage, or a complication thereof, is provided, wherein the compound is a compound described herein, or a pharmaceutically acceptable salt thereof.

In some embodiments, this disclosure provides a method of treating a spinal cord injury or damage, or a complication thereof, in a patient, comprising administering to a patient in need thereof a therapeutically effective amount of a compound of formula I or Ia:

I

Ia

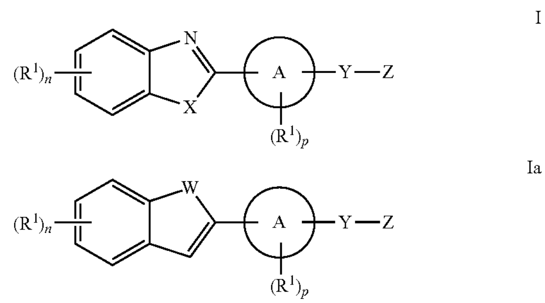

or a pharmaceutically acceptable salt, solvate, and/or an N-oxide thereof, wherein:

subscripts n and p are independently selected from 0, 1 or 2;

each $R^1$ is independently selected from the group consisting of hydrogen, halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro;

A is an arylene or heteroarylene, having 1 to 4 heteroatoms;

W is selected from the group consisting of —O—, —S—, —SO—, $—S(O)_2—$, and $—NR^2—$, wherein $R^2$ is selected from the group consisting of hydrogen, alkyl, substituted alkyl, aryl, substituted aryl, heteroaryl, substituted heteroaryl, heterocyclyl, and substituted heterocyclyl;

X is selected from the group consisting of —O—, —S—, —SO—, $—S(O)_2—$, and $—NR^2—$, provided that when A is arylene, and Y is —S— or $—NR^2—$, then X is not —S—;

Y is selected from the group consisting of —O—, —S—, —SO—, $S(O)_2$—, and —$NR^2$—; and Z is selected from the group consisting of —$N(CH_3)_2$ $CH_2CH_2OC(O)CH_3$ and —$(CH_2CH(R^3)O)_q$-T, wherein subscript q is an integer selected from 1 to 100, $R^3$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate.

In some embodiments of the methods described herein, A is phenylene or pyridylene in the compound of formula I or Ia. In some embodiments, X is S in the compound of formula I. In some embodiments, Y is —O— in the compound of formula I or Ia. In some embodiments, X is S, Y is —O—, and A is phenylene in the compound of formula I.

In some embodiments of the methods described herein, the compound of formula I is a compound of formula Ik:

Ik

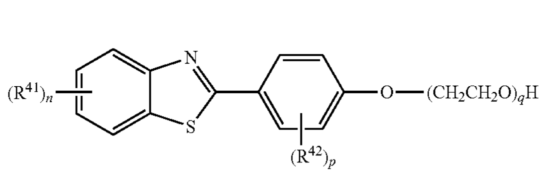

or a pharmaceutically acceptable salt, solvate, and/or an N-oxide thereof, wherein:

subscripts n and p are each independently 0, 1, or 2;

subscript q is an integer from 2 to 8; and each $R^{41}$ and each $R^{42}$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

In some embodiments of the methods described herein, each of subscripts n and p is 0 in the compounds of formula Ik.

In some embodiments of the methods described herein, the compound of formula I is:

Compound 1

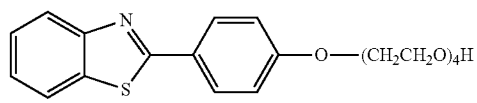

or a pharmaceutically acceptable salt, solvate, and/or an N-oxide thereof.

In some embodiments, this disclosure provides a method of treating a spinal cord injury or damage, or a complication thereof, in a patient, comprising administering to a patient in need thereof a therapeutically effective amount of a compound of formula II:

II

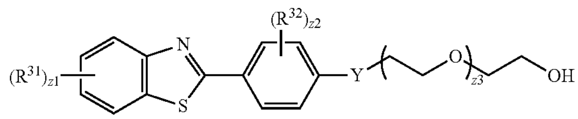

or a pharmaceutically acceptable salt, solvate, and/or an N-oxide thereof, wherein:

Y is —$NR^{33}$— or —S—;

each $R^{31}$ is independently halogen, —$CX^{31}$, —$CHX^{31}$, —$CH_2X^{31}$, —$OCX^{31}_3$, —$OCHX^{31}_2$, —$OCH_2X^{31}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$C(O)NHNH_2$, —$NHC(O)NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

each $R^{32}$ is independently halogen, —$CX^{32}_3$, —$CHX^{32}_2$, —$CH_2X^{32}$, —$OCX^{32}_3$, —$OCHX^{32}_2$, —$OCH_2X^{32}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

$R^{33}$ is H, alkyl, or substituted alkyl;

each of $X^{31}$ and $X^{32}$ is independently halogen;

each of z1 and z2 is independently an integer from 0 to 4; and z3 is an integer from 1 to 12.

In some embodiments of the methods described herein, Y is S in the compound of formula II. In some embodiments, each of z1 and z2 is 0 in the compound of formula II.

In some embodiments of the methods described herein, the compound of formula II is:

Compound 2

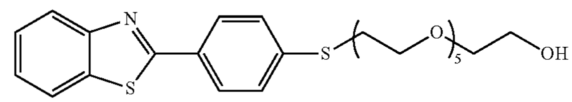

or a pharmaceutically acceptable salt or solvate thereof.

In some embodiments of the methods described herein, Y is NH in the compound of formula II. In some embodiments, z1 is 1 , z2 is 0, and $R^{31}$ is alkyl in the compound of formula II.

In some embodiments of the methods described herein, the compound of formula II is:

Compound 3

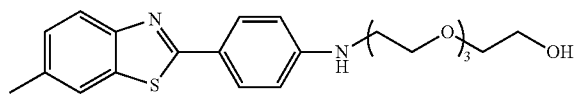

or a pharmaceutically acceptable salt, solvate, and/or an N-oxide thereof.

In some embodiments, this disclosure provides a method of treating a spinal cord injury or damage, or a complication thereof, in a patient, wherein the complication of spinal cord injury or damage is a respiratory complication, cardiovascular complication, hypotension, bradycardia, neurogenic shock, an autonomic dysreflexia, secondary immunodeficiency, syringomyelia, neuropathic joint arthropathy, Charcot joint arthropathy, loss of motor control, loss of sensory function, tetraplegia, paraplegia, loss of bladder control, spasm, loss of sexual function, numbness, loss of balance, autonomic dysreflexia, deep vein thrombosis, spasticity, pain, neuropathic pain, syringomyelia, neurogenic heterotopic ossification, shock, bradyarrhythmias, hypotension, ectopic beats, abnormal temperature regulation, changes in sweat secretion, vasodilatation, autonomic dysreflexia, thromboembolism, pressure ulcer, or heterotopic ossification, or a combination thereof.

In some embodiments, this disclosure provides a method of treating a spinal cord injury or damage, or a complication thereof, in a patient, wherein the patient has Chiari malformation, radiculopathy, hydrocephalus, or neuropathy due to infections. In some embodiments, the neuropathy due to infections is from Lyme disease.

Compounds

Provided herein are agents that promote spinogenesis. Such agents are surprisingly found to be useful in the treatment of mood disorders. The agent may be a compound provided herein.

The compound may be a compound described in International Patent Publication No. WO 2019/028164. In some embodiments, the compound is a compound of formula I or formula Ia:

I

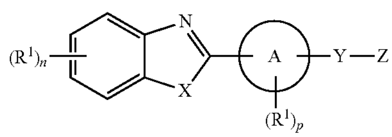

Ia

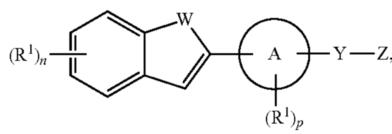

or a pharmaceutically acceptable salt, solvate, and/or an N-oxide thereof, wherein:

subscripts n and p are independently selected from 0, 1 or 2;

each $R^1$ is independently selected from the group consisting of hydrogen, halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro;

A is an arylene or heteroarylene, having 1 to 4 heteroatoms;

W is selected from the group consisting of —O—, —S—, —SO—, —$S(O)_2$—, and —$NR^2$—, wherein $R^2$ is selected from the group consisting of hydrogen, alkyl, substituted alkyl, aryl, substituted aryl, heteroaryl, substituted heteroaryl, heterocyclyl, and substituted heterocyclyl;

X is selected from the group consisting of —O—, —S—, —SO—, —$S(O)_2$—, and —$NR^2$—, wherein $R^2$ is as defined above, provided that when A is arylene, and Y is —S— or —$NR^2$—, then X is not —S—;

Y is selected from the group consisting of —O—, —S—, —SO—, $S(O)_2$—, and —$NR^2$—, wherein $R^2$ is as defined above; and Z is selected from the group consisting of —$N(CH_3)_2$ $CH_2CH_2OC(O)CH_3$ and —$(CH_2CH(R^3)O)_q$-T, wherein subscript q is an integer from 1 to 100, $R^3$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate.

In some embodiments, this disclosure provides a compound of formula I or Ia, wherein A is phenylene or pyridylene. In some embodiments, X is S in the compound of formula I. In some embodiments, Y is —O— in the compound of formula I or Ia. In some embodiments, X is S, Y is —O—, and A is phenylene in the compound of formula I.

In some embodiments, provided is a compound according to Formula Ib, Formula Ic, Formula Id, Formula Ie, and/or Formula Ig:

Ib

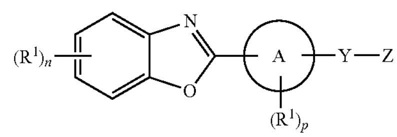

Ic

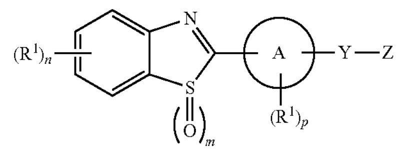

Id

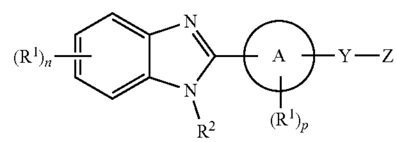

Ie

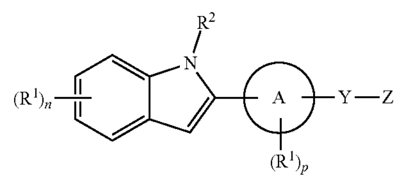

Ig

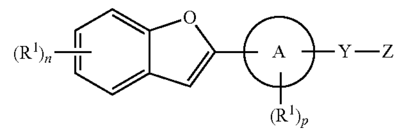

or a pharmaceutically acceptable salt, solvate, and/or an N-oxide thereof, wherein:

$R^1$, $R^2$, A, Y, Z, n and p are as defined above with respect to formula I and formula Ia; and subscript m is 0, 1 or 2.

In some embodiments, provided is a compound selected from:

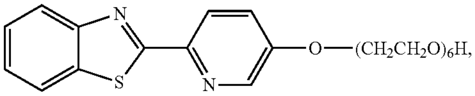

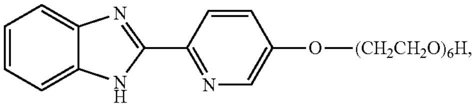

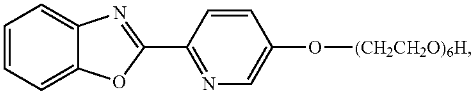

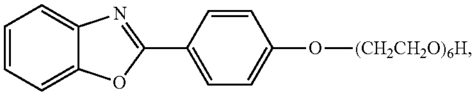

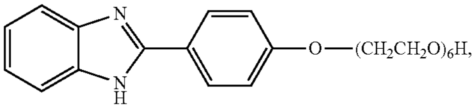

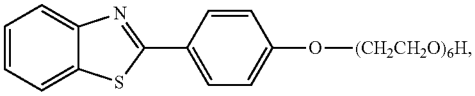

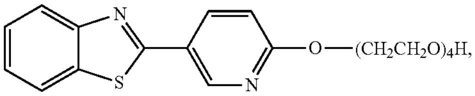

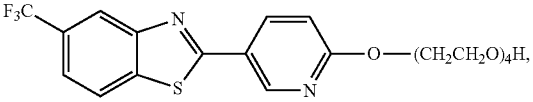

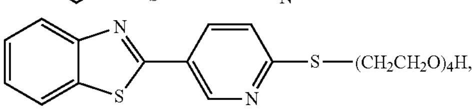

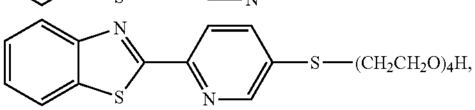

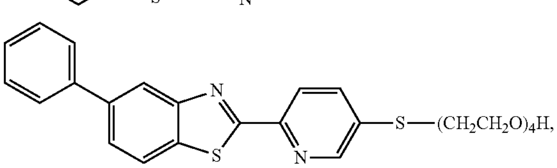

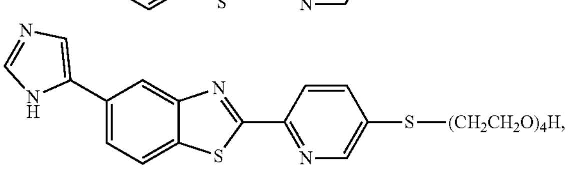

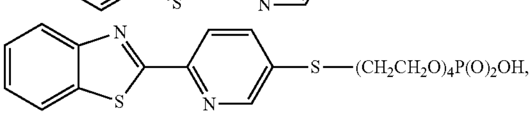

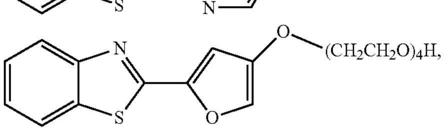

-continued

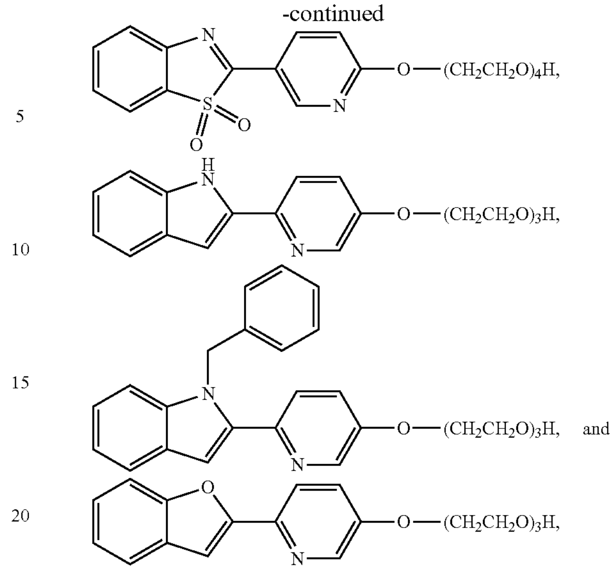

and or a pharmaceutically acceptable salt, solvate, and/or an N-oxide thereof.

In some embodiments, the compound is a compound of formula Ik:

Ik

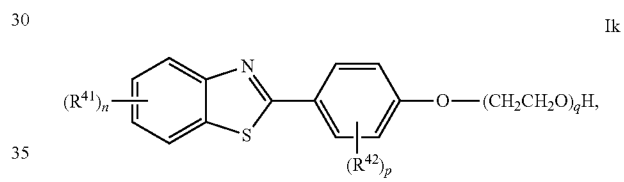

or a pharmaceutically acceptable salt, solvate, and/or an N-oxide thereof, wherein:

subscripts n and p are each independently 0, 1 or 2;

subscript q is an integer from 2 to 8; and each $R^{41}$ and each $R^{42}$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

In some embodiments, this disclosure provides compounds of formula Ik, wherein each of subscripts n and p is 0.

In some embodiments, provided is a compound, or a pharmaceutically acceptable salt, solvate, and/or an N-oxide thereof, as described herein, selected from:

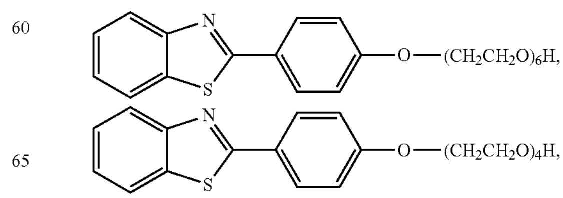

-continued
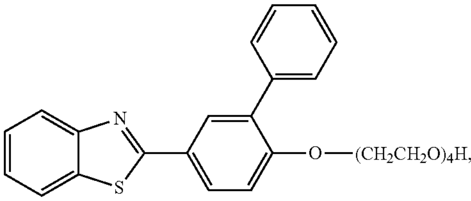,
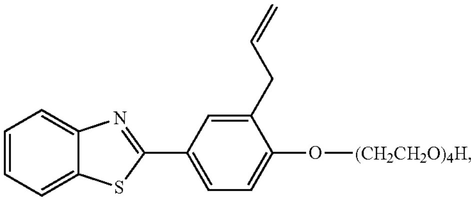,
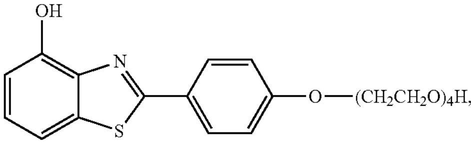,
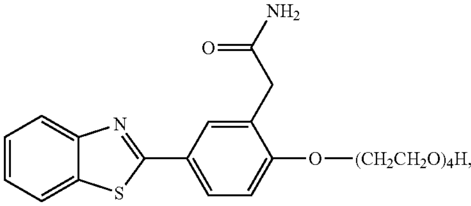,
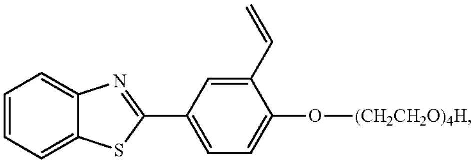,
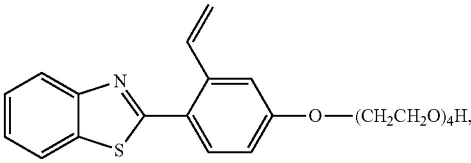,
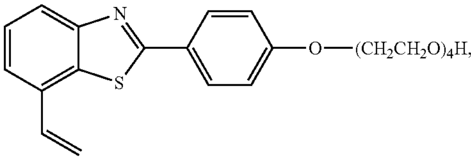,
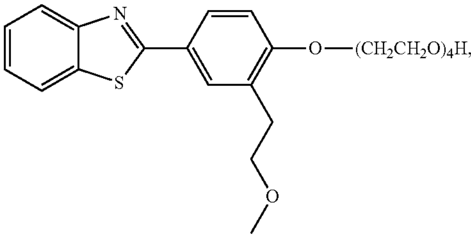,
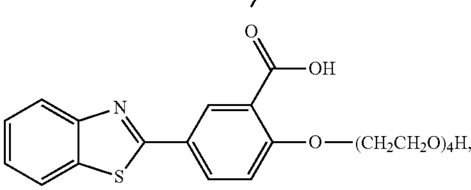,
-continued
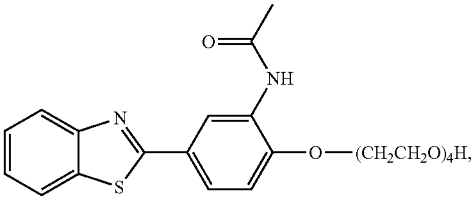,
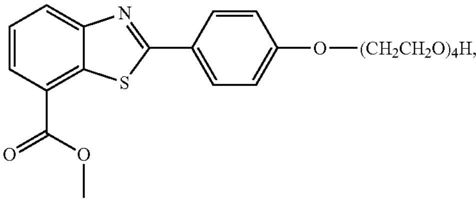,
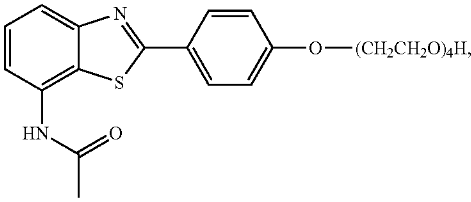,
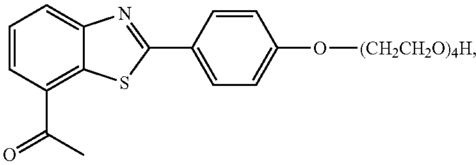,
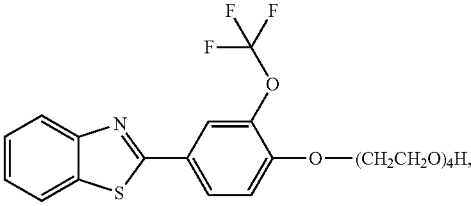,
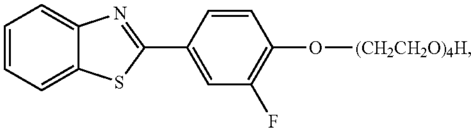,
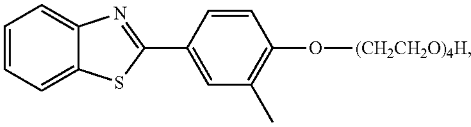,
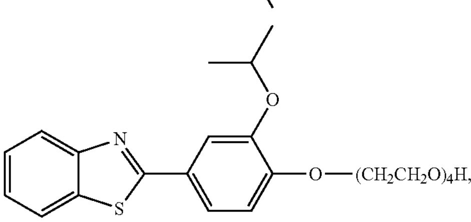,
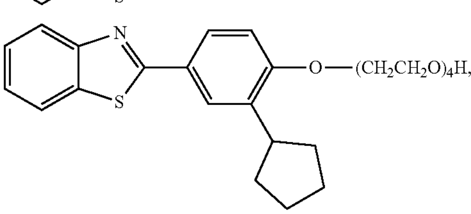, -continued
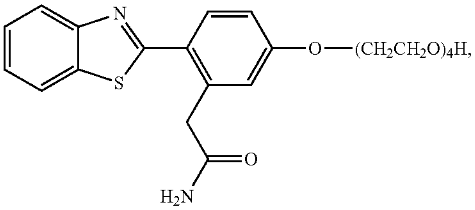
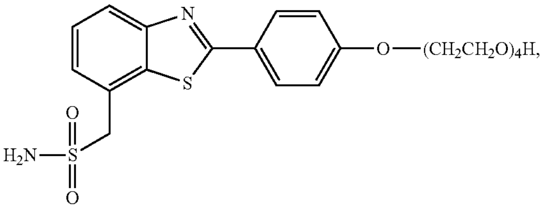
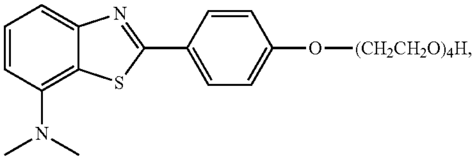
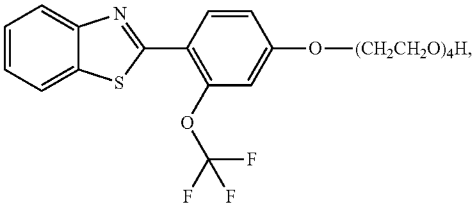
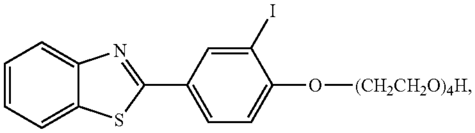
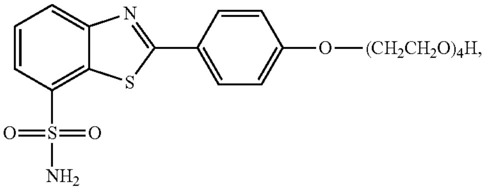
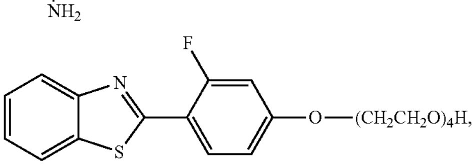
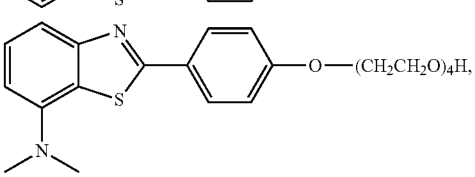
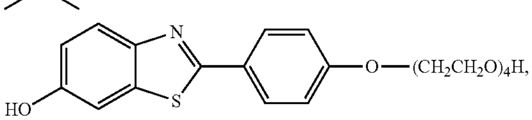
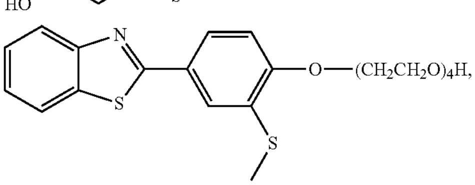
-continued
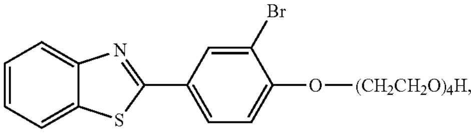
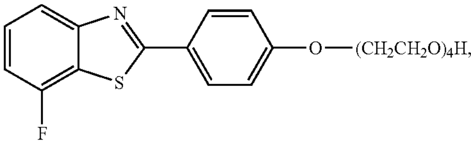
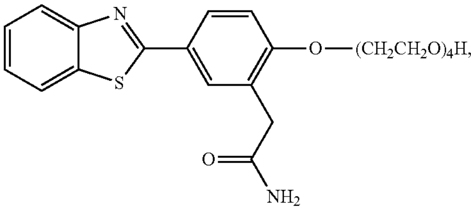
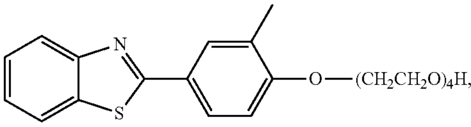
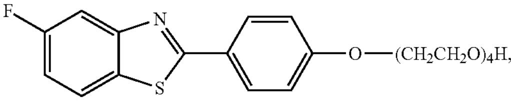
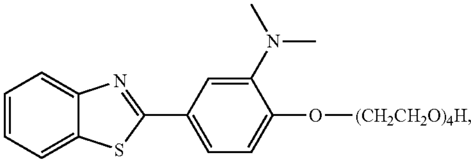
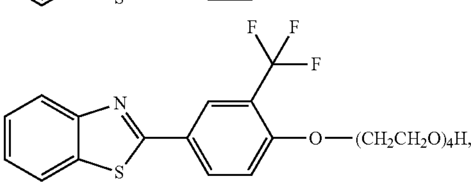
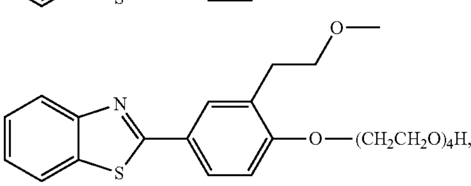
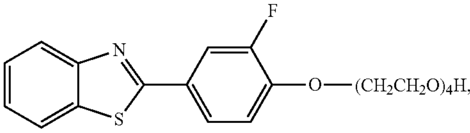
and
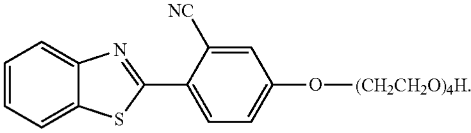
In some embodiments, provided is a compound according to Formula Ij:

(Ij)

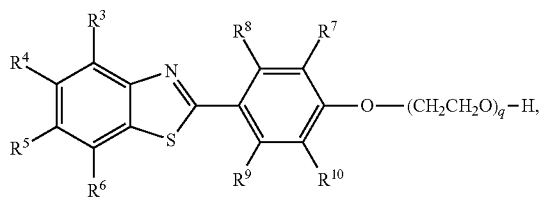

or a pharmaceutically acceptable salt, solvate, and/or an N-oxide thereof, wherein:

subscript q is an integer from 4 or 6;

$R^3$, $R^4$, $R^5$, and $R^6$ are independently selected from the group consisting of hydrogen halo, —$CH_3$, and —$OCH_3$; and $R^7$, $R^8$, $R^9$, and $R^{10}$ are independently selected from the group consisting of hydrogen, halo, —$CH_3$, —$CF_3$, —$OCH_3$, —$OCF_3$, phenyl, and —$NO_2$;

wherein at least six of $R_3$-$R_{10}$ are hydrogen.

In some embodiments, provided is a compound, or a pharmaceutically acceptable salt, solvate, and/or an N-oxide thereof, selected from:

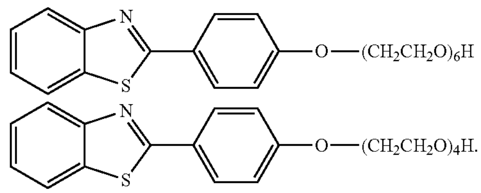

and

In some embodiments, the compound is

Compound 1

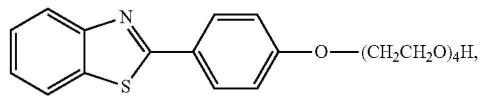

or a pharmaceutically acceptable salt, solvate, and/or an N-oxide thereof.

In some embodiments, the compound is a compound described in International Publication No. WO 2017/120198. In some embodiments, the compound is a compound of formula II:

II

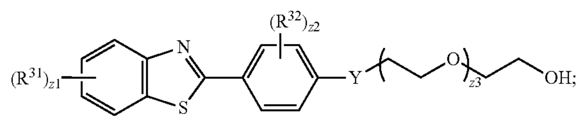

or a pharmaceutically acceptable salt, solvate, and/or an N-oxide thereof, wherein:

Y is —$NR^{33}$—, or —S—;

$R^{31}$ is independently halogen, —$CX^{31}$, —$CHX^{31}$, —$CH_2X^{31}$, —$OCX^{31}{}_3$, —$OCHX^{31}{}_2$, —$OCH_2X^{31}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —C(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;;

each $R^{32}$ is independently halogen, —$CX^{32}{}_3$, —$CHX^{32}{}_2$, —$CH_2X^{32}$, —$OCX^{32}{}_3$, —$OCHX^{32}{}_2$, —$OCH_2X^{32}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

$R^{33}$ is H, alkyl, or substituted alkyl;

each of $X^{31}$ and $X^{32}$ is independently halogen;

each of z1 and z2 is independently an integer from 0 to 4; and z3 is an integer from 1 to 12.

In some embodiments, this disclosure provides a compound of formula II, wherein Y is S. In some embodiments, each of z1 and z2 is 0.

In some embodiments, the compound is a compound of formula IIa:

Iia

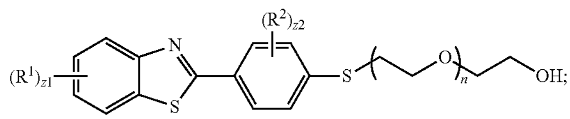

or a pharmaceutically acceptable salt, solvate, and/or an N-oxide thereof, wherein:

each $R^1$ is independently halogen, —$CX^1{}_3$, —$CHX^1{}_2$, —$CH_2X^1$, —$OCX^1{}_3$, —$OCHX^1{}_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

each $R^2$ is independently halogen, —$CX^2{}_3$, —$CHX^2{}_2$, —$CH_2X^2$, —$OCX^2{}_3$, —$OCHX^2{}_2$, —$OCH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;;

each of $X^1$ and $X^2$ is independently halogen;

each of z1 and z2 is independently an integer from 0 to 4; and n is an integer from 1 to 12.

In some embodiments, the compound is

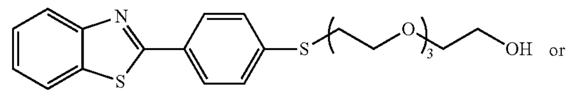

or

-continued

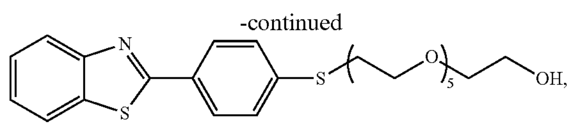

or a pharmaceutically acceptable salt, solvate, and/or an N-oxide thereof.

In some embodiments, the compound is

Compound 2

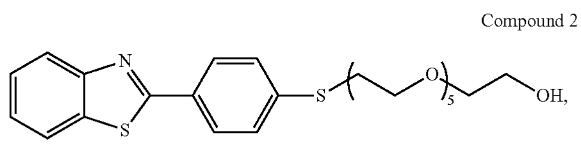

or a pharmaceutically acceptable salt, solvate, and/or an N-oxide thereof.

In some embodiments, this disclosure provides a compound of formula II, wherein Y is NH or NMe. In some embodiments, z1 is 1 , z2 is 0, and $R^{31}$ is alkyl.

In some embodiments, the compound is

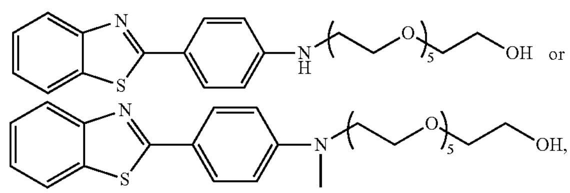

or a pharmaceutically acceptable salt, solvate, and/or an N-oxide thereof.

In some embodiments, the compound is

Compound 3

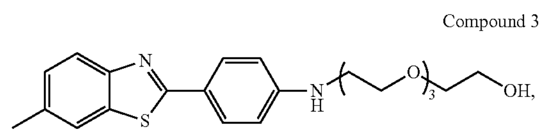

or a pharmaceutically acceptable salt, solvate, and/or an N-oxide thereof.

In some embodiments, the compound is a compound described in U.S. Pat. No. 8,741,883. In some embodiments, the compound is a compound of formula III:

III

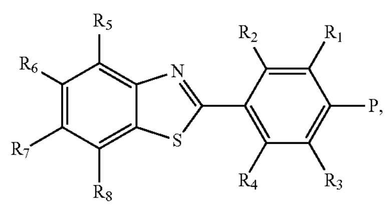

or a pharmaceutically acceptable salt, solvate, and/or an N-oxide thereof, wherein:

$R_1$-$R_8$ are selected from the group consisting of hydrogen, deuterium, tritium, fluoro, chloro, bromo, iodo, hydroxyl, amino, methylamino, dimethylamino, trimethylammonium, methyl, ethyl, methoxy, ethoxy, fluoromethyl, difluoromethyl, and trifluoromethyl, wherein at least one of $R_5$-$R_8$ and one of $R_1$-$R_4$ is H; and P is selected from the group consisting of

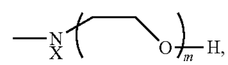

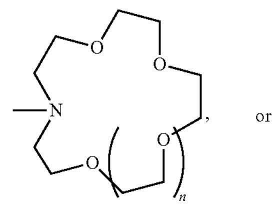

, or

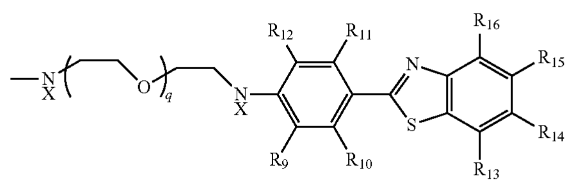

wherein:

m is an integer from 1 and 20;

n is 0, 1, or 2; q is an integer from 1 and 20;

$R_9$-$R_{16}$ are selected from the group consisting of hydrogen, deuterium, tritium, fluoro, chloro, bromo, iodo, hydroxyl, amino, methylamino, dimethylamino, trimethylammonium, methyl, ethyl, methoxy, ethoxy, fluoromethyl, difluoromethyl, and trifluoromethyl, wherein at least one of $R_9$-$R_{12}$ and one of $R_{13}$-$R_{16}$ is H; and X is hydrogen, methyl, or ethyl.

In some embodiments, the compound of formula III is a compound of formula IIIa:

IIIa

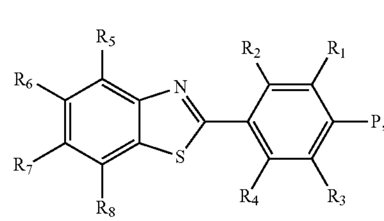

or a pharmaceutically acceptable salt, solvate, and/or an N-oxide thereof, wherein:

$R_1$-$R_8$ are selected from the group consisting of hydrogen, deuterium, tritium, fluoro, chloro, bromo, iodo, hydroxyl, amino, methylamino, dimethylamino, trimethylammonium, methyl, ethyl, methoxy, ethoxy, fluoromethyl, difluoromethyl, and trifluoromethyl, wherein at least one of $R_5$-$R_8$ and one of $R_1$-$R_4$ is H; and P is:

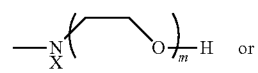

or

-continued

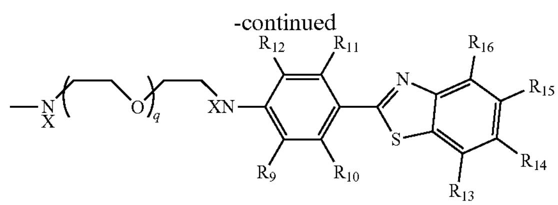

wherein m is an integer from 1 and 20;

q is an integer from 1 and 20;

$R_9$-$R_{16}$ are selected from the group consisting of hydrogen, deuterium, tritium, fluoro, chloro, bromo, iodo, hydroxyl, amino, methylamino, dimethylamino, trimethylammonium, methyl, ethyl, methoxy, ethoxy, fluoromethyl, difluoromethyl, and trifluoromethyl, wherein at least one of $R_9$-$R_{12}$ and one of $R_{13}$-$R_{16}$ is H; and X is hydrogen, methyl, or ethyl.

In some embodiments, the compound is selected from:

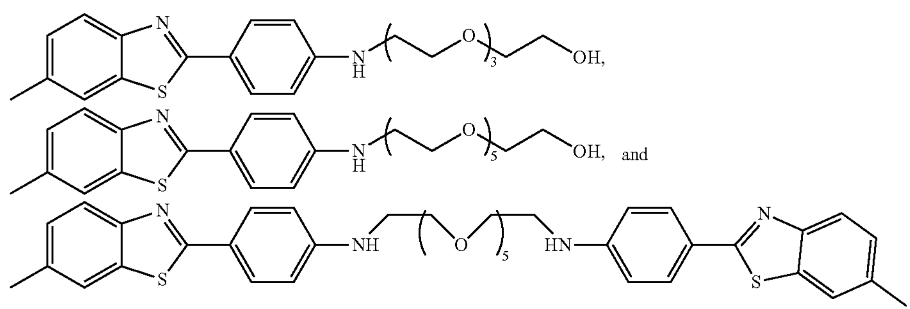

or a pharmaceutically acceptable salt, solvate, and/or an N-oxide thereof.

Combination Therapies

In one embodiment, the compounds disclosed herein may be used in combination with one or more additional therapeutic agent that are being used and/or developed to treat a SCI, When used for the treatment of the diseases and disorders described above, a compound described herein, or a pharmaceutically acceptable salt thereof, may be administered together with one or more additional therapeutic agents, for example additional therapeutic agents approved for use in the treatment of the particular disease or disorder, and more particularly agents considered to form the current standard of care. Where combination therapy is envisaged, the active agents may be administered simultaneously, separately or sequentially; and may be administered together in a single pharmaceutical composition, or in more than one pharmaceutical composition.

A compound described herein, or a pharmaceutically acceptable salt thereof, may be administered in combination with one or more additional therapies used in treatment of spinal cord injury or damage, or a complication thereof. The one or more additional therapies may be a drug therapy, a non-drug therapy, or a combination thereof.

Non-drug therapies include, for example, limb or stabilization; alignment; traction, for example, Halo traction or Gardner-Wells Tongs traction; bracing, for example, or the head and/or neck; mechanical ventilation; physical therapy; and surgery.

Kits

Provided herein are also kits that include compounds described herein, or a pharmaceutically acceptable salt thereof, optionally a second active ingredient, and suitable packaging. In one embodiment, a kit further includes instructions for use. In one aspect, a kit includes a compound, or a pharmaceutically acceptable salt thereof, and a label and/or instructions for use of the pharmaceutical composition in the treatment of the indications, including the diseases or conditions, described herein.

Provided herein are also articles of manufacture that include a compound described herein, or a pharmaceutically acceptable salt thereof in a suitable container. The container may be a vial, jar, ampoule, preloaded syringe, nebulizer, aerosol dispensing device, dropper, or intravenous bag.

Pharmaceutical Compositions and Modes of Administration

Compounds provided herein are usually administered in the form of pharmaceutical compositions. Thus, provided herein are also pharmaceutical compositions that contain a compound described herein, or a pharmaceutically acceptable salt thereof and one or more pharmaceutically acceptable excipients. Suitable pharmaceutically acceptable excipients may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G.S. Banker & C.T. Rhodes, Eds.).

The pharmaceutical compositions may be administered in either single or multiple doses. The pharmaceutical composition may be administered by various methods including, for example, rectal, buccal, intranasal and transdermal routes. In certain some embodiments, the pharmaceutical composition may be administered by intra-arterial injection, intravenously, intraperitoneally ("i.p."), parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compositions described herein. Administration may be via, for example, capsule or enteric coated tablets. In making the pharmaceutical compositions that include at least one compound described herein or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical composition and any container in which it is distributed may be sterilized. The pharmaceutical composition may also contain adjuvants such as preservatives, stabilizers, emulsifiers or suspending agents, wetting agents, salts for varying the osmotic pressure, viscosity alerting agents, or buffers.

The compositions that include at least one compound described herein, such as a compound described herein, or a pharmaceutically acceptable salt thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The pharmaceutical composition may be formulated for nasal administration. Such pharmaceutical compositions may include one or more active ingredients, such as a compound described herein, or a pharmaceutically acceptable salt thereof, in varying physical states. For example, the active ingredients may be dissolved or suspended in a liquid carrier. The active ingredients may be in a dry form. The dry form may be a powder. Active ingredients in a powder may be amorphous or crystalline. For example, a compound described herein, or a pharmaceutically acceptable salt thereof, may be amorphous or crystalline. The crystalline active material may be a hydrate or a solvate.

Solid compounds, or a salt or crystal thereof, may be present in a formulation in a selected average particle size. The particles may have an average particle size (in longest dimension) of 10 nm, 100 nm, 300 nm, 500 nm, 1 μm, 10 μm, 50 μm, 100 μm, 300 μm, or 500 μm, or a range between any two values.

Administration may be by inhalation or insufflation. Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route. Effects may be local or systemic. In a particular embodiment, the effect is local to cranial tissues. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner. A pharmaceutical composition for inhalation or insufflation may be an aerosol.

The pharmaceutical composition may comprise a liquid suspension or solution comprising about 0.05%, about 0.1%, about 0.3%, about 0.5%, about 0.7%, about 1%, about 2%, about 3%, about 4%, or about 5% w/w of active ingredients. The liquid may comprise water and/or an alcohol. The liquid may include a pH adjusting agent such that the pH is about 1, about 2, about 3, about 4, about 5, about 6, about 7, about 8, about 9, or about 10, or a range of values therebetween.

The pharmaceutical composition may comprise a pharmaceutically acceptable preservative. Preservatives suitable for use herein include, but are not limited to, those that protect the solution from contamination with pathogenic particles, including phenylethyl alcohol, benzalkonium chloride, benzoic acid, or benzoates such as sodium benzoate. In certain some embodiments, the pharmaceutical composition comprises from about 0.01% to about 1.0% w/w of benzalkonium chloride, or from about 0.01% and about 1% v/w phenylethyl alcohol. Preserving agents may also be present in an amount from about 0.01% to about 1%, preferably about 0.002% to about 0.02% by total weight or volume of the composition.

The pharmaceutical composition may also comprise from about 0.01% to about 90%, or about 0.01% to about 50%, or about 0.01% to about 25%, or about 0.01% to about 10%, or about 0.01% to about 1% w/w of one or more of an emulsifying agent, a wetting agent or a suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methyl cellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerized fatty acids of soya bean oil; oxidatively polymerized soya bean oil; and pectin extract.

In a further embodiment, the pharmaceutical composition for nasal administration may be provided in the form of a powder. For example, a powdery nasal composition can be directly used as a powder for a unit dosage form. If desired, the powder can be filled in capsules such as hard gelatine capsules. The contents of the capsule or single dose device may be administered using e.g. an insufflator.

Thus, a method for treating a neuronal disorder may include the step of administering nasally a pharmaceutical composition comprising a compound described herein, or a salt thereof, to a subject in need thereof.

Dosing

The specific dose level of an active ingredient of the present application, for example a compound described herein, of a salt thereof, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.01 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound described herein, or a salt thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered nasally, the total daily dosage for a human subject may be between about 1 mg and 1,000 mg, between about 1,000-2,000 mg/day, between about 10-500 mg/day, between about 50-300 mg/day, between about 75-200 mg/day, or between about 100-150 mg/day. In various embodiments, the daily dosage is about 10 mg, about 30 mg, about 50 mg, about 75 mg, about 100 mg, about 200 mg, about 300 mg, about 400 mg, about 500 mg, about 600 mg, about 700 mg, about 800 mg, about 900 mg, or about 1000 mg, or a range of values therebetween.

The active ingredients of the present application or the pharmaceutical compositions thereof may be administered once, twice, three, or four times daily, using any suitable mode described above. Also, administration or treatment may be continued for a number of days; for example, commonly treatment would continue for at least 7 days, 14 days, or 28 days, for one cycle of treatment The treatment cycles, may be continuous. Administration or treatment may be continued indefinitely.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

In the specification and in the examples below, the following abbreviations have the following meanings. If not defined, these abbreviations have their art recognized meaning.

BDNF=brain-derived neurotrophic factor
CTB=cholera toxin subunit beta
DMSO=dimethylsulfoxide
EMG=electromyography
NMJ=neuromuscular junction
TrkB=tropomyosin receptor kinase B
C2HS

EXAMPLES

Example 1

Hypothesis: A compound described herein will ameliorate the functional and pathological diaphragm motor unit deficits following unilateral cervical spinal cord hemisection (C2HS), compared to vehicle treated C2HS rats.

Outcome Measures: Serial diaphragm EMG, serial ventilatory transdiaphragmatic (Pdi) pressures, terminal maximum Pdi, ex vivo assessment of glutamatergic inputs on phrenic motor neurons.

Experimental Groups: This would involve 3 cohorts of animals; I—Vehicle treated C2HS rats (12), II—compound treated C2HS rats (12) and III—Sham surgery+compound treated rats (6).

Statistical Comparisons: For functional recovery, we powered sample sizes based on past observations of ~18% spontaneous recovery 14 days post-SH. We expect similar levels of recovery improvement to other neurotrophic agents tested in the lab (e.g. BDNF/TrkB), which increase recovery to ~67%. For ex vivo pathology measures, differences in glutamatergic inputs within SH rats (comparing lesioned and non-lesioned sides) required 8 rats, and across animal sham comparisons, 6.

Phrenic motor neurons are identified via bilateral intrapleural labelling of CTB. It is anticipated that any size-dependent motor neuron loss in the SOD1 rodent model to be detected using this technique, similar to loss observed in aged rats.

Diaphragm muscle (DIAm) EMG activity is recorded independently for either side of the diaphragm. Eupnea (quiet breathing), with raw traces (bursts) and RMS (root-mean square—an estimate of EMG magnitude) are calculated for each burst. In the cervical spinal hemisection model, EMG activity during eupnea may be abolished ipsilateral to the lesion.

Transdiaphragmatic (Pdi) pressure is calculated from the sum of the negative intrathoracic pressure and the positive intra-abdominal pressure, as measured in the oesophagus (Peso) and gastric (Pgas) spaces, respectively. The maximum Pdi, elicited via bilateral phrenic nerve stimulation (blue box) gives a reliable upper estimate of diaphragm neuromotor function in vivo. In conditions where motor unit specific loss of motor neurons occurs (such as in ALS), maximum Pdi is observed to be impaired, while ventilatory Pdi remains relatively unaffected.

The number and density of glutamatergic inputs onto labelled phrenic motor neurons is estimated. Following the C2HS procedure, motor neurons that receive ipsilateral ventilatory drive from the medulla exhibit a marked loss of glutamatergic inputs, compared to the control (non-lesioned) side. Treatment using a compound described herein post-injury lessens the deficit.

Neuromuscular transmission failure (NMTF) is the contribution of axon propagation failures and/or NMJ synaptic infidelity to muscle fatigue. Over a 120 s period, NMTF contributes to the waning force production, with direct muscle stimulation evoked forces remaining stable. The NMTF is exacerbated by age, due to both the denervation (leading to axon propagation failures) and NMJ morphological impairments (less apposition of pre- and post-synaptic elements of the NMJ). With aging, the derangement of pre-synaptic (synaptophysin and neurofilament) and post-synaptic regions (bungarotoxin) only occurs in the fatigable (type Iix and/or IIb) fibers. It is determined that in SOD1 rats, a similar pattern of functional loss and pathology is present. It is further determined that type I, type IIa and type IIx and/or IIb diaphragm muscle fibers shows atrophy in only the type IIx and/or IIb fibers of old compared to young rats. A similar pattern of pathology is determined to obtain in SOD1 ALS model rats.

Example 2

To demonstrate the efficacy of the compounds for treating spinal cord injury or damage, the effect of the benzothiazole compounds on synaptic puncta and synapses of mouse cortical neurons is investigated.

Primary mouse cortical neurons are treated with 5 μM of a compound described herein at DIV 15. As a control, primary mouse cortical neurons are treated with the vehicle only (10% DMSO, 90% phosphate buffered saline (PBS)). After 24 hours, the DIV 16 neurons are fixed, immunostained using the presynaptic vesicle protein synaptophysin (P38), counterstained with the nuclear dye DAPI (4',6-diamidino-2-phenylindole,), and counted. Immunolabeled neurons are imaged on a Leica confocal microscope. The numbers of P38-immunopositive puncta are analyzed using FIJI with the Squash plugin. Compounds described herein are observed to cause an increase in the number of synaptic puncta compared to the vehicle control.

In a similar experiment, the primary mouse cortical neurons are treated with 1 μM of compound at DIV 15, using the same DMSO/PBS buffer solution described above as the control vehicle. After 24 hours, the DIV 16 neurons are fixed, immunolabeled with synaptophysin, stained with DAPI, and counted as described above. After 24 hrs, the compound is observed to promote about a 100% increase in the number of synapses when compared to the control.

Example 3

A representative compound of this disclosure, Compound 1, was used in treating spinal cord injury in rats. The rat C2 hemisection (C2HS) model of spinal cord injury was used in this experiment. The spinal cord injury was modeled in rats by hemi-section at the level of C2 followed by monitoring of lesion and recovery was conducted by one of the following methods: diaphragm EMG, transdiaphragmatic pressure, and ventilatory behaviors.

Figure 1B:
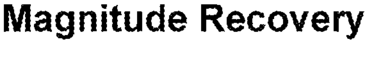
Figure 1B:
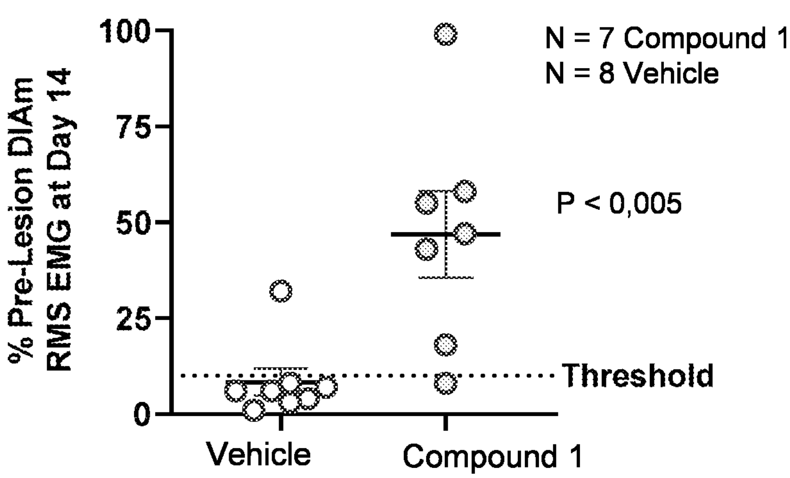

Seven rats were treated with Compound 1 (30 mg/kg) and 8 rats were treated with a vehicle (0.5% DMSO in phosphate buffered saline) for 14 days and their recovery was monitored. It was found that 86% of the rats treated with Compound 1 recovered as judged by diaphragm EMG by day 14 post lesion. Also, the magnitude of recovery was an average 54% among recovered compound-treated rats as compared to vehicle-treated rats. The recovery was greater than that seen for brain derived neurothrophic factor approaches. The results are shown in FIGS. 1A and 1B.

Similar experiment was carried out separately using 4 rats and it provided similar results as those described above. Specifically, it provided greater % recovery and greater magnitude of recovery with rats treated with Compound 1 as compared to vehicle-treated rats.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method of treating a spinal cord injury or damage, or a complication thereof, in a patient, comprising administering to a patient in need thereof a therapeutically effective amount of a compound of formula I or Ia:

I

Ia

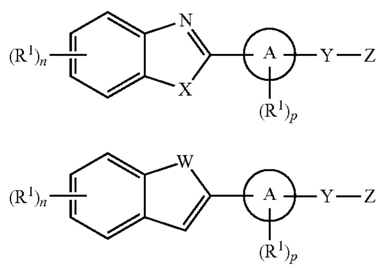

or a pharmaceutically acceptable salt, solvate, and/or an N-oxide thereof, wherein:

subscripts n and p are independently selected from 0, 1, or 2;

each $R^1$ is independently selected from the group consisting of hydrogen, halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro;

A is an arylene or heteroarylene, having 1 to 4 heteroatoms;

W is selected from the group consisting of —O—, —S—, —SO—, —$S(O)_2$—, and —$NR^2$—, wherein $R^2$ is selected from the group consisting of hydrogen, alkyl, substituted alkyl, aryl, substituted aryl, heteroaryl, substituted heteroaryl, heterocyclyl, and substituted heterocyclyl;

X is selected from the group consisting of —O—, —S—, —SO—, —$S(O)_2$—, and —$NR^2$—, provided that when A is arylene, and Y is —S— or —$NR^2$—, then X is not —S—;

Y is selected from the group consisting of —O—, —S—, —SO—, $S(O)_2$—, and —$NR^2$—; and Z is selected from the group consisting of —$N(CH_3)CH_2CH_2OC(O)CH_3$ and —$(CH_2CH(R^3)O)_q$-T, wherein subscript q is an integer selected from 1 to 100, $R^3$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate; and wherein the complication of spinal cord injury or damage is a respiratory complication, cardiovascular complication, hypotension, bradycardia, neurogenic shock, an autonomic dysreflexia, secondary immunodeficiency, syringomyelia, neuropathic joint arthropathy, Charcot joint arthropathy, loss of motor control, loss of sensory function, tetraplegia, paraplegia, loss of bladder control, spasm, loss of sexual function, numbness, loss of balance, autonomic dysreflexia, deep vein thrombosis, spasticity, pain, neuropathic pain, syringomyelia, neurogenic heterotopic ossification, shock, bradyarrhythmias, hypotension, ectopic beats, abnormal temperature regulation, changes in sweat secretion, vasodilatation, autonomic dysreflexia, thromboembolism, pressure ulcer, or heterotopic ossification, or a combination thereof.

2. The method of claim 1, wherein A is phenylene or pyridylene in the compound of formula I or Ia.

3. The method of claim 1, wherein X is S in the compound of formula I.

4. The method of claim 1, wherein Y is —O— in the compound of formula I or Ia.

5. The method of claim 1, wherein X is S, Y is —O—, and A is phenylene in the compound of formula I.

6. The method of claim 1, wherein the compound of formula I is a compound of formula Ik:

Ik

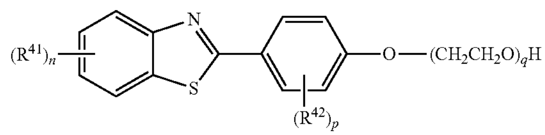

or a pharmaceutically acceptable salt, solvate, and/or an N-oxide thereof, wherein:

subscripts n and p are each independently 0, 1, or 2;

subscript q is an integer from 2 to 8; and each $R^{41}$ and each $R^{42}$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

7. The method of claim 5, wherein each of subscripts n and p is 0.

8. The method of claim 5, wherein the compound of formula I is:

Compound 1

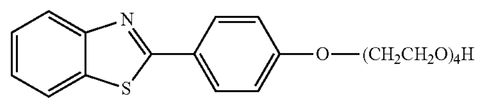

or a pharmaceutically acceptable salt, solvate, and/or an N-oxide thereof.

9. A method of treating a spinal cord injury or damage, or a complication thereof, in a patient, comprising administering to a patient in need thereof a therapeutically effective amount of a compound of formula II:

II

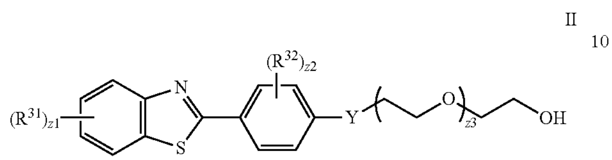

or a pharmaceutically acceptable salt, solvate, and/or an N-oxide thereof, wherein:

Y is —$NR^{33}$— or —S—;

each $R^{31}$ is independently halogen, —$CX^{31}_3$, —$CHX^{31}_2$, —$CH_2X^{31}$, —$OCX^{31}_3$, —$OCHX^{31}_2$, —$OCH_2X^{31}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —C(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

each $R^{32}$ is independently halogen, —$CX^{32}_3$, —$CHX^{32}_2$, —$CH_2X^{32}$, —$OCX^{32}_3$, —$OCHX^{32}_2$, —$OCH_2X^{32}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, alkyl, substituted alkyl, heteroalkyl, substituted heteroalkyl, cycloalkyl, substituted cycloalkyl, heterocyclyl, substituted heterocyclyl, aryl, substituted aryl, heteroaryl, or substituted heteroaryl;

$R^{33}$ is H, alkyl, or substituted alkyl;

each of $X^{31}$ and $X^{32}$ is independently halogen;

each of z1 and z2 is independently an integer from 0 to 4; and z3 is an integer from 1 to 12; and wherein the complication of spinal cord injury or damage is a respiratory complication, cardiovascular complication, hypotension, bradycardia, neurogenic shock, an autonomic dysreflexia, secondary immunodeficiency, syringomyelia, neuropathic joint arthropathy, Charcot joint arthropathy, loss of motor control, loss of sensory function, tetraplegia, paraplegia, loss of bladder control, spasm, loss of sexual function, numbness, loss of balance, autonomic dysreflexia, deep vein thrombosis, spasticity, pain, neuropathic pain, syringomyelia, neurogenic heterotopic ossification, shock, bradyarrhythmias, hypotension, ectopic beats, abnormal temperature regulation, changes in sweat secretion, vasodilatation, autonomic dysreflexia, thromboembolism, pressure ulcer, or heterotopic ossification, or a combination thereof.

10. The method of claim 9, wherein Y is S.

11. The method of claim 9, wherein each of z1 and z2 is 0.

12. The method of claim 9, wherein the compound of formula II is:

Compound 2

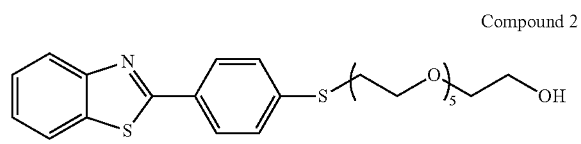

or a pharmaceutically acceptable salt, solvate, and/or an N-oxide thereof.

13. The method of claim 9, wherein Y is NH.

14. The method of claim 9, wherein z1 is 1, z2 is 0, and $R^{31}$ is alkyl.

15. The method of claim 9, wherein the compound of formula II is:

Compound 3

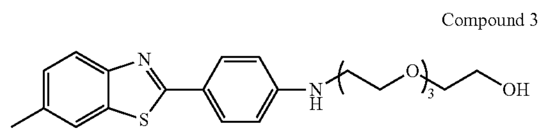

or a pharmaceutically acceptable salt, solvate, and/or an N-oxide thereof.

16. The method of claim 1, wherein the patient has Chiari malformation, radiculopathy, hydrocephalus, or neuropathy due to infections.

17. The method of claim 16, wherein the neuropathy due to infections is from Lyme disease.

* * * * *